United States Patent

Capik et al.

[11] Patent Number: 5,354,597
[45] Date of Patent: Oct. 11, 1994

[54] ELASTOMERIC TAPES WITH MICROTEXTURED SKIN LAYERS

[75] Inventors: Karen M. Capik, Woodbury, Minn.; Dennis L. Krueger, Hudson, Wis.; Joaquin Delgado, St. Paul, Minn.

[73] Assignee: Minnesota Mining and Manufacturing Company, St. Paul, Minn.

[21] Appl. No.: 985,740

[22] Filed: Dec. 4, 1992

Related U.S. Application Data

[63] Continuation of Ser. No. 744,675, Aug. 9, 1991, abandoned, which is a continuation of Ser. No. 502,329, Mar. 30, 1990, abandoned.

[51] Int. Cl.[5] .................................... C09J 7/02
[52] U.S. Cl. .................................... 428/152; 428/343; 428/354
[58] Field of Search ............... 428/152, 198, 230, 231, 428/343, 354; 604/385.2, 389, 390

[56] References Cited

U.S. PATENT DOCUMENTS

| | | | |
|---|---|---|---|
| 2,559,990 | 7/1951 | Oace et al. | 428/337 |
| 2,951,277 | 9/1960 | Youngs | 428/175 |
| 3,252,833 | 5/1966 | Skobel | 428/297 |
| 3,253,073 | 5/1966 | Skobel | 164/174 |
| 3,265,765 | 8/1966 | Holden et al. | 525/271 |
| 3,365,315 | 1/1968 | Beck et al. | 106/40 |
| 3,379,562 | 4/1968 | Freeman | 428/40 |
| 3,479,425 | 11/1969 | Lefevre et al. | 264/171 |
| 3,483,018 | 12/1969 | Waldman | 428/286 |
| 3,557,265 | 1/1971 | Chilholm et al. | 264/47 |
| 3,562,356 | 2/1971 | Nyberg et al. | 525/93 |
| 3,618,754 | 11/1971 | Hoey | 206/411 |
| 3,691,140 | 9/1972 | Silver | 526/240 |
| 3,700,633 | 10/1972 | Wald et al. | 525/339 |
| 3,800,796 | 4/1974 | Jacob | 604/390 |
| 3,819,401 | 6/1974 | Massengale et al. | 156/85 |
| 3,857,731 | 12/1974 | Merrill, Jr. et al. | 428/314.4 |
| 4,024,312 | 5/1977 | Korpman | 428/343 |
| 4,074,716 | 2/1978 | Schaar . | |
| 4,116,917 | 9/1978 | Eckert | 585/11 |
| 4,152,387 | 5/1979 | Cloeren | 264/171 |
| 4,156,673 | 5/1979 | Eckert | 524/534 |
| 4,181,752 | 1/1980 | Martens et al. | 427/54.1 |
| 4,237,889 | 12/1980 | Gobran | 604/389 |
| 4,386,125 | 5/1983 | Shiraki et al. | 428/36 |
| 4,389,212 | 6/1983 | Tritsch | 604/389 |
| 4,476,180 | 10/1984 | Wnuk | 428/220 |
| 4,522,853 | 6/1985 | Szonn et al. | 428/40 |
| 4,525,407 | 6/1985 | Ness | 428/138 |
| 4,568,344 | 2/1986 | Suzuki et al. | 604/389 |
| 4,643,729 | 2/1987 | Laplanche | 604/389 |
| 4,684,685 | 8/1987 | Shuman et al. | 524/270 |
| 4,698,242 | 10/1987 | Salerno | 427/208.2 |
| 4,767,726 | 8/1988 | Marshall | 501/33 |
| 4,778,701 | 10/1988 | Pape et al. | 428/40 |
| 4,787,897 | 11/1988 | Torimae et al. | 604/389 |
| 4,795,456 | 1/1989 | Borgers et al. | 604/390 |
| 4,813,946 | 3/1989 | Sabee | 604/385.2 |
| 4,813,947 | 3/1989 | Korpman | 604/387 |
| 4,834,820 | 5/1989 | Kondo et al. | 156/73.3 |
| 4,861,635 | 8/1989 | Carpenter et al. | 604/390 X |
| 4,880,682 | 11/1989 | Hazelton et al. | 428/152 |
| 4,935,287 | 6/1990 | Johnson et al. | 428/198 |
| 5,057,097 | 10/1991 | Gesp | 604/389 |

FOREIGN PATENT DOCUMENTS

| | | | |
|---|---|---|---|
| WO90/02540 | 3/1990 | PCT Int'l Appl. | A61F 13/16 |
| 1264196 | 7/1969 | United Kingdom | B32B 25/08 |
| 2160473A | 12/1986 | United Kingdom | B29C 55/00 |

Primary Examiner—Jenna L. Davis
Attorney, Agent, or Firm—Gary L. Griswold; Walter N. Kirn; William J. Bond

[57] ABSTRACT

Microtextured elastomeric laminate tape comprising a laminate with at least one elastomeric layer and at least one thin skin layer, and an adhesive layer, preferably prepared by coextrusion of the layers followed by stretching the laminate past the elastic limit of the skin layers and then allowing the laminate tape to recover.

20 Claims, 9 Drawing Sheets

ELASTOMERIC TAPES WITH MICROTEXTURED SKIN LAYERS

This is a continuation of application Ser. No. 07/744,675 filed Aug. 9, 1991, now abandoned, which is a continuation of application Ser. No. 502,329 now abandoned.

FIELD OF THE INVENTION

The invention concerns elastomeric tape end more specifically concerns tape laminates. These tape laminates are particularly useful in garment applications.

BACKGROUND

Elastomeric tapes are known and used for a variety of purposes. The most common use of elastomeric tapes is as a stretchable backing for a bandage. This is discussed in, e.g., U.S. Pat. No. 3,618,754 (Hoey), which describes a composite structure using a woven layer having elastomeric warp yarns interspersed with flexible warp yarns, the cross or filler yarns are exemplified as cotton. The elastomeric yarns are preferably an elastomeric Spandex TM core with a rayon spun outer covering. This tape is complex and difficult to manufacture. Other constructions for bandage tapes are likewise complex with many designed to provide controlled modulus behavior. Namely, a tape is preferred that has only a limited degree of extensibility and then a high modulus value.

Elastomeric tapes have also been proposed for use as electrical insulating tapes based on the electrical properties of rubber as well as their ability to grip a surface, i.e. with their recovery forces when applied under stress. These types of elastic tapes are described, for example, in U.S. Pat. Nos. 3,379,562, 2,559,990 and 3,253,073, which are all described as insulating tapes.

U.S. Pat. No. 2,559,990 describes a basic elastic tape of an elastic film forming polymer with a rubber-resin adhesive coating. The elastomer is described as a plasticized vinyl chloride with a blend of plasticizers in permanent equilibrium with a rubber resin adhesive. When this tape is wound into a roll form a liner is used. This liner must be removed when the tape is used to allow it to adhere to itself.

Elimination of this removable liner is proposed in U.S. Pat. No. 3,379,562, which places a barrier layer on the tape backside which shatters when stretched. This allegedly exposes the rubber and allows tape to adhere to itself when the tape is stretched. However, fragments of the barrier layer can still interfere with adhesion of the tape to itself.

U.S. Pat. No. 3,253,073 describes a tape allegedly designed for high temperature performance. The tape substrate is a laminate of two insulating rubber layers sandwiching a fiber layer. The fibers are brittle and when the tape is stretched sufficiently the fibers break, thereby making the tape elastic in the stretch direction. These fibers are used to improve high temperature performance.

A purely elastomeric tape was also disclosed in U.S. Pat. No. 4,024,312 although no specific uses are proposed. The tape comprises a ABA block copolymer based rubber substrate with a rubber resin adhesive on one side and a release coat on the other. The high extensibility allegedly allows the tape to be easily removed when peeled at substantially 0°. This is stated as a desirable quality for ouchless bandages.

Elastic tapes or tapes with elasticized regions have also been proposed as closures for diapers, and the like, in U.S. Pat. Nos. 4,389,212, 3,800,796, 4,643,729, 4,778,701 and 4,834,820. In U.S. Pat. No. 4,834,820, an elastic tab is provided with either a removable central section or a inelastic cover layer adhered at only the ends of the elastic. When the removable section is removed, the elastic loses its support and is free to stretch. With an unattached central portion of a cover layer, the central portion has a line of weakness which when broken frees the central elastic region. U.S. Pat. No. 4,778,701 also provides an elasticized central region in a composite tape. An elastic strip is adhered to two nonelastomeric anchor strip tapes used to attach either side of the diaper. Complex constructions having features of the above two patents are described in U.S. Pat. Nos. 4,643,729 and 4,389,212. U.S. Pat. No. 3,800,796 describes tapes with elasticized central portions and rigid ends with adhesive layers. All of these tapes are complex multicomponent composites aimed at providing only limited elastic central tape portions.

SUMMARY OF THE INVENTION

The present invention relates to non-tacky, microtextured, multi-layer elastomeric laminated tapes. The laminate tape backings of the present invention are comprised both of an elastomeric polymeric core layer(s), which provides elastomeric properties to the laminate and one or more polymeric skin layers which are capable of becoming microtextured. This microtexturing gives the tape natural low adhesion backsize properties, increases ink receptivity, acts as an adhesive primer, and lowers the laminate coefficient of friction and modulus. In preferred embodiments of the present invention the skin layer further can function to permit controlled release or recovery of the stretched elastomer, modify the modulus of elasticity of the elastomeric tape and/or stabilize the shape of the elastomeric tape (i.e., by controlling further necking). The laminate tape backings can be prepared by coextrusion of the selected polymers or by application of one or more elastomer layers onto one or more already formed skin layer(s) or vice versa. Coextrusion is preferred. Pressure-sensitive adhesive (hereinafter adhesive) can be applied by any conventional mechanism including coextrusion. The novel microtextured laminate tape and/or tape backing is obtained by stretching the laminate past the elastic limit of the skin layers. The laminate then recovers, which can be instantaneous, over an extended time period, which is skin layer controllable, or by the application of heat, which is also skin layer controllable.

Stretching of the laminate tape or backing can be uniaxial, sequentially biaxial, or simultaneously biaxial. It has been found that the method and degree of stretch allows significant control over the microtextured surface that results, allowing formation of novel surfaces and adhesion properties. The invention thus further provides various novel surfaces and also a method for the controlled production of these surfaces.

DETAILED DESCRIPTION OF PREFERRED EMBODIMENTS OF THE INVENTION

Figure 1:
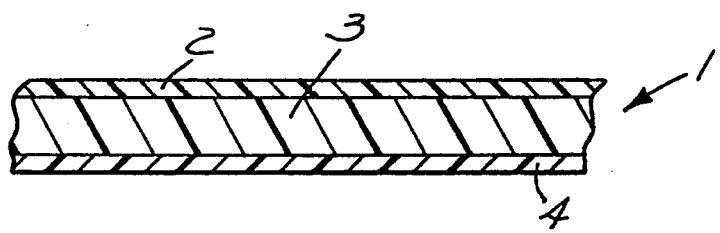
FIG. 1 is a cross-sectional segment of an extruded laminate tape backing 1 before microstructuring.

The present invention relates broadly to novel tape using a non-tacky, multi-layer elastomeric laminate backing comprising at least one elastomeric layer and at least one relatively nonelastomeric skin layer. The skin layer is stretched beyond its elastic limit and is relaxed with the core so as to form a microstructured surface. Microstructure means that the surface contains peak and valley irregularities or folds which are large enough to be perceived by the unaided human eye as causing increased opacity over the opacity of the laminate before microstructuring, and which irregularities are small enough to be perceived as smooth or soft to human skin. Magnification of the irregularities is required to see the details of the microstructured texture.

The elastomer can broadly include any material which is capable of being formed into a thin film layer and exhibits elastomeric properties at ambient conditions. Elastomeric means that the material will substantially resume its original shape after being stretched. Further, preferably, the elastomer will sustain only small permanent set following deformation and relaxation which set is preferably less than 20 percent and preferably less than 10 percent of the original length at moderate elongation, e.g., about 400–500%. Generally, any elastomer is acceptable which is capable of being stretched to a degree that causes relatively consistent permanent deformation in a relatively inelastic skin layer. This can be as low as 50% elongation. Preferably, the elastomer is capable of undergoing up to 300 to 1200% elongation at room temperature, and most preferably up to 600 to 800% elongation at room temperature. The elastomer can be both pure elastomers and blends with an elastomeric phase or content that will still exhibit substantial elastomeric properties at room temperature.

Heat-shrinkable elastics have received considerable attention due to the ability to attach the elastic to a product, using the unstable stretched elastomer at ambient conditions, and then later applying heat to shirr the product, such as a diaper. Although these elastomers are contemplated for use in the present invention tape, other non-heat shrinkable elastomers can be used while retaining the advantages of heat shrinkability and with the added dimension of the possibility of substantially controlling the heat shrink process. Non-heat shrinkable means that the elastomer, when stretched, will substantially recover sustaining only a small permanent set as discussed above. Therefore, the elastomeric layer can be formed from non-heat-shrinkable polymers such as block copolymers which are elastomeric such as those known to those skilled in the art as A-B or A-B-A block copolymers. Such copolymers are described for example in U.S. Pat. Nos. 3,265,765; 3,562,356; 3,700,633; 4,116,917 and 4,156,673, the substance of which is incorporated herein by reference. Styrene/isoprene, butadiene or ethylene-butylene/styrene (SIS, SBS or SEBS) block copolymers are particularly useful. Other useful elastomeric compositions can include elastomeric polyurethanes, ethylene copolymers such as ethylene vinyl acetates, ethylene/propylene monomer copolymer elastomers or ethylene/propylene/diene terpolymer elastomers. Blends of these elastomers with each other or with modifying non-elastomers are also contemplated. For example, up to 50 weight percent, but preferably less than 30 weight percent, of polymers can be added as stiffening aids such as polyvinylstyrenes, polystyrenes such as poly(alpha-methyl)styrene, polyesters, epoxies, polyolefins, e.g., polyethylene or certain ethylene/vinyl acetates, preferably those of higher molecular weight, or coumarone-indene resin. The ability to use these types of elastomers and blends provides the invention laminate with significant flexibility.

Viscosity reducing polymers and plasticizers can also be blended with the elastomers such as low molecular weight polyethylene and polypropylene polymers and copolymers, or tackifying resins such as Wingtack ™, aliphatic hydrocarbon tackifiers available from Goodyear Chemical Company. Tackifiers can also be used to increase the adhesiveness of an elastomeric layer to a skin layer. Examples of tackifiers include aliphatic or aromatic liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric core layer(s). Suitable antistatic aids include ethoxylated amines or quaternary amines such as those described, for example, in U.S. Pat. No. 4,386,125 (Shiraki), who also describes suitable antiblocking agents, slip agents and lubricants. Softening agents, tackifiers or lubricants are described, for example, in U.S. Pat. No. 4,813,947 (Korpman) and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate. Suitable antioxidants include hindered phenolic compounds and amines possibly with thiodipropionic acid or aromatic phosphates or tertiary butyl cresol, see also U.S. Pat. No. 4,476,180 (Wnuk) for suitable additives and percentages.

Short fibers or microfibers can be used to reinforce the elastomeric layer for certain applications. These fibers are well known and include polymeric fibers, mineral wool, glass fibers, carbon fibers, silicate fibers and the like. Further, certain particles can be used, including carbon and pigments.

Glass bubbles or foaming agents are used to lower the density of the elastomeric layer and can be used to reduce cost by decreasing elastomer content required. These agents can also be used to increase the bulk of the elastomer. Suitable glass bubbles are described in U.S. Pat. Nos. 4,767,726 and 3,365,315. Foaming agents used to generate bubbles in the elastomer include azodicarbonamides. Fillers can also be used to some extent to reduce costs. Fillers, which can also function as antiblocking agents, include titanium dioxide and calcium carbonate.

The skin layer can be formed of any semi-crystalline or amorphous polymer that is less elastic than the core layer(s) and will undergo permanent deformation at the stretch percentage that the elastomeric laminate will undergo. Therefore, slightly elastic compounds, such as some olefinic elastomers, e.g. ethylene-propylene elastomers or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate)(only in blends) and the like, and blends thereof. The skin layer material can be influenced by the type of elastomer selected. If the elastomeric layer is in direct contact with the skin layer the skin layer should have sufficient adhesion to the elastomeric core layer such that it will not readily delaminate. Acceptable skin-to-core contact has been found to follow three modes: first, full contact between core and microtextured skin; second, cohesive failure of the core under the microstructure folds; and third, adhesive failure of the skin to the core under the microstructure folds with intermittent skin/core contact at the fold valleys. However, where a high modulus elastomeric layer is used with a softer polymer skin layer attachment may be adequate yet a microtextured surface may not form.

The skin layer is used in conjunction with an elastomeric layer and can either be an outer layer or an inner layer (e.g., sandwiched between two elastomeric layers). Used as either an outer or inner layer the skin layer will modify the elastic properties of the elastomeric laminate.

Additives useful in the skin layer include, but are not limited to, mineral oil extenders, antistatic agents, pigments, dyes, antiblocking agents, provided in amounts less than about 15%, starch and metal salts for degradability and stabilizers such as those described for the elastomeric core layer.

Other layers may be added between the core layer and the outer layers, such as tie layers to improve the bonding of the layers. Tie layers can be formed of, or compounded with, typical compounds for this use including maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatibilizers in one or more of the skin or core layers. Tie layers are particularly useful when the bonding force between the skin and core is low. This is often the case with polyethylene skin as its low surface tension resists adhesion. However, any added layers must not significantly affect the microstructuring of the skin layers. Tie layers may, however, be omitted even when bonding between skin and core is low. For example, for tamper indicating tapes, low adhesion delamination can be used advantageously.

One unique feature of the invention is the ability to control the shrink recovery mechanism of the tape depending on the conditions of film formation, the nature of the elastomeric layer, the nature of the skin layer, the manner in which the laminate tape backing is stretched and the relative thicknesses of the elastomeric and skin layer(s). By controlling these variables in accordance with the teaching of this invention the laminate tape or backing can be designed to instantaneously recover, recover over time or recover upon heat activation.

A laminate capable of instantaneous shrink is one in which the stretched elastomeric laminate will recover more than 15% in 1 sec. A laminate capable of time shrink is one where the 15% recovery point takes place more than 1 sec., preferably more than 5 sec., most preferably more than 20 sec. after stretch, and a laminate capable of heat shrink is where less than 15% shrink recovery occurs to the laminate in the first 20 seconds after stretch. Percent recovery is the percent that the amount of shrinkage is of the stretched length minus the original length. For heat shrink, there will be an activation temperature which will initiate significant heat activated recovery. The activation temperature used for heat shrink will generally be the temperature that will yield 50% of the total possible recovery ($T_{a\text{-}50}$) and preferably this temperature is defined as the temperature which will yield 90% ($T_{a\text{-}90}$) of the total possible recovery. Total possible recovery includes the amount of preactivation shrinkage.

Generally, where the skin layer of the laminate tape backing is relatively thin, the laminate will tend to contract or recover immediately. When the skin thickness is increased sufficiently the laminate can become heat shrinkable. This phenomenon can occur even when the elastomeric layer is formed from a non-heat shrinkable material. Further, by careful selection of the thicknesses of the elastomeric layer and the skin layer(s), the temperature at which the laminate recovers by a set amount can be controlled within a set range. This is termed skin controlled recovery where generally by altering the thickness or composition of the skin, one can raise the activation temperature of an elastomeric core by a significant degree, generally more than at least 10° F. (5.6° C.) and preferably by 15° F. (8.3° C.) and more. Although any skin thickness which is effective can be employed, too thick a skin will cause the laminate to remain permanently set when stretched. Generally, where a single skin is less than 30% of the laminate this will not occur. For most heat or time shrink materials the stretched elastomer must be cooled so that the energy released during stretching does not cause immediate heat activated recovery. Fine tuning of the shrink recovery mechanism can be accomplished by the amount of stretch. This overall control over the shrink recovery mechanism can be an extremely important advantage, for example, when the unactivated tape is used in a manufacturing process. This control permits adjustment of the recovery mechanism of the elastomeric laminate tape to fit the requirements of a manufacturing process rather than the need to adjust a manufacturing process to fit the shrink recovery mechanism of the elastomer itself.

One is also able to use skin controlled recovery to control the slow or time shrink recovery mechanism, as with the heat shrink mechanism. This shrink recovery mechanism occurs as an intermediate between instant and heat shrink recovery. Skin layer and stretch ratio control of recovery is possible as in the heat shrink mechanism, with the added ability to change the shrink mechanism in either direction, i.e., to a heat or an instant shrink elastomeric laminate tape.

A time shrink recovery laminate tape will also exhibit some heat shrink characteristics and vice versa. For example, a time shrink laminate tape can be prematurely recovered by exposure to heat, e.g., at a time prior to 20 seconds after stretch.

Recovery can also be initiated for most time shrink and some low activation temperature heat shrink recovery laminates by mechanical deformation or activation. In this case, the laminate tape is scored, folded, wrinkled, or the like to cause localized stress fractures that cause localized premature folding of the skin, accelerating formation of the recovered microtextured laminate. Mechanical activation can be performed by any suitable method such as by using a textured roll, a scoring wheel, mechanical deformation or the like.

It was also noted that for most elastomeric laminates over a core skin ratio of about 3 to somewhat above 7, the laminate retained a relatively constant width after it had been restretched. Specifically, if the width of the stretched and recovered film is measured, and if the film is restretched and measured or allowed to recover again and measured, the width remains within at least 20% of its first measured stretch width, preferably within at least 10%. This non-necking characteristic helps prevent the laminate tape from biting into the skin of a wearer when it is used to elasticize a garment or become dimensionally unstable when used as an electrical, wrapping or removable tape, which may cause pop off, tape slippage or the like. Generally, the skin layer will hinder the elastic force of the core layer with a counteracting resisting force. The skin will not stretch with the elastomer after the laminate has been activated, the skin will simply unfold into a rigid sheet. This reinforces the core, resisting or hindering the contraction of the elastomeric core including its necking tendency.

Figure 12:
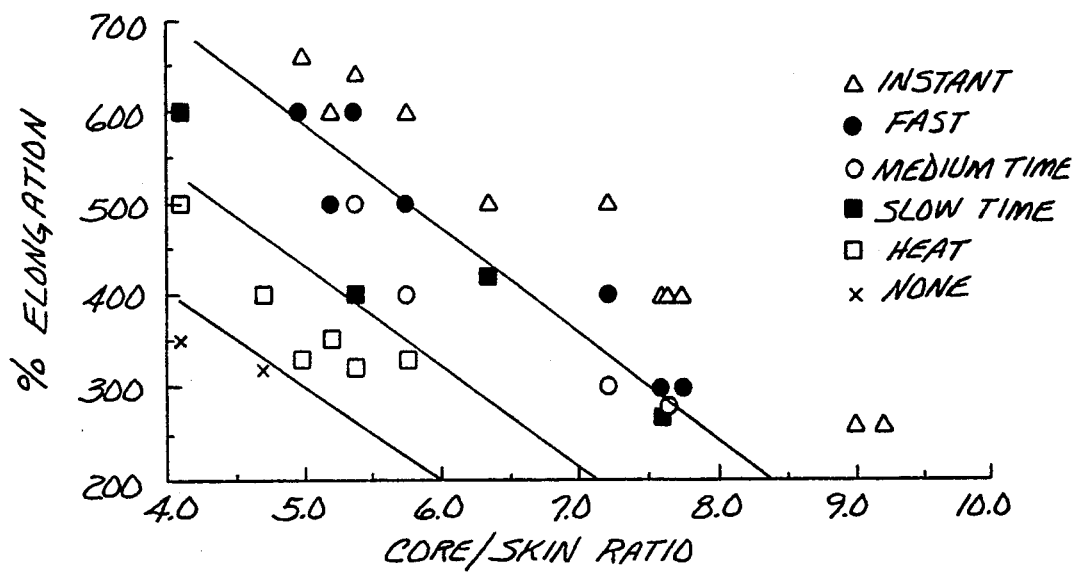
FIG. 12 is a diagram showing the relationship between the shrink mechanism and the core/skin ratio and stretch ratio for a second uniaxially stretched film.

FIG. 12 shows a shrink mechanism diagram for polypropylene/styrene-isoprene-styrene (SIS)/polypropylene(PP) laminates prepared in accordance with Example 29. This diagram demonstrates the ability to control the shrink recovery mechanism by the skin/core ratio and the stretch ratio.

Although FIG. 12 is illustrative of a particular set of starting materials and thicknesses, it does represent the general relationship between the layer ratios and stretch ratio to the shrink mechanism of the laminate. Other variables will affect the above relationship such as overall laminate thickness, the presence of tie layers and the thickness and type of adhesive layer. However, the general relationship between the core/skin ratio and the stretch ratio to the relaxation method will still be present.

Additives to the core layer discussed above can significantly affect the shrink recovery mechanism. For example, stiffening aids such as polystyrene can shift an otherwise heat shrinkable laminate into a time or instant shrink laminate. However, the addition of polypropylene or linear low density polyethylene (less than 15%) to a styrene/isoprene/styrene block copolymer core resulted in exactly the opposite effect, namely transforming time or instant shrink laminates to heat shrink or no shrink laminates. However, the possibility of polyolefin use in the elastomeric core layer is significant from a processing standpoint in permitting limited recycling of off batches and it can lower extruder torque.

A further unique feature of the present invention lies in the ability to significantly reduce the coefficient of friction (C.O.F.) of the elastomeric laminate. The microtexturing is the major factor contributing to this C.O.F. reduction which, as discussed above, is controllable not only by the manner in which the laminate is stretched but also by the degree of stretch, the overall laminate thickness, the laminate layer composition and the core to skin ratio. The dependence of C.O.F. on core/skin ratio is shown in Table II, as the ratio increases the C.O.F. decreases. Thus, fine texture yields lower C.O.F. values. Preferably, the C.O.F., to itself, will be reduced by a factor of 0.5 and most preferably by at least a factor of 0.1 of the microtextured laminate to itself in the direction of stretch, when a microstructured surface is formed in accordance with the invention, as compared to the as cast laminate. This ability to reduce C.O.F. is extremely advantageous as it contributes to a softer texture and feel for the laminate, which is desirable for use in the medical and apparel fields.

Figure 7:
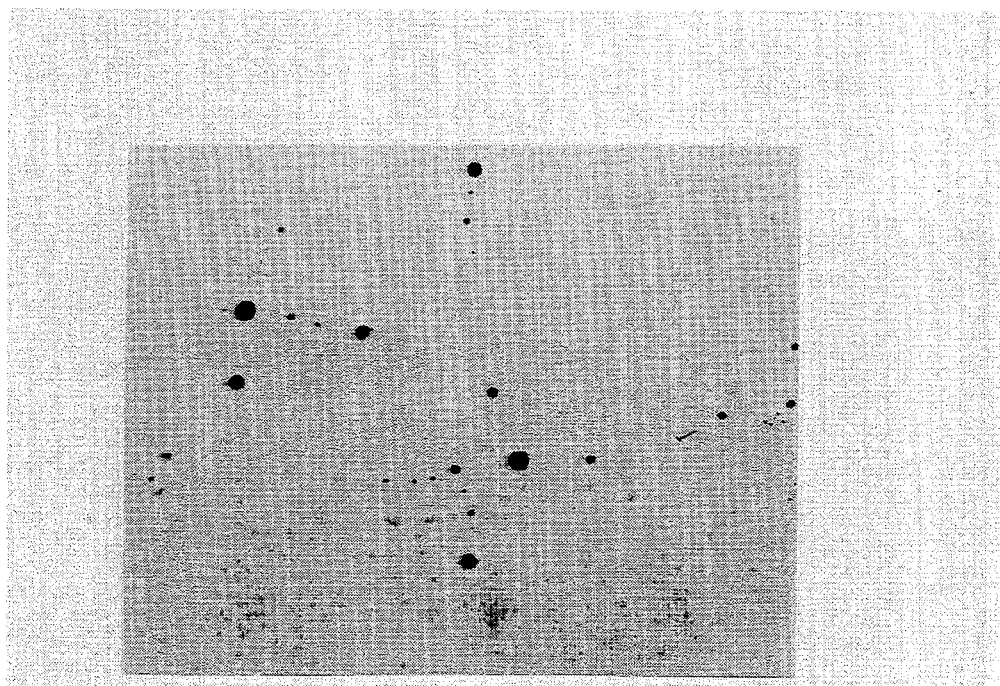
FIG. 7 is a photograph of an unstretched laminate tape backing that has been marked with ink.
Figure 8:
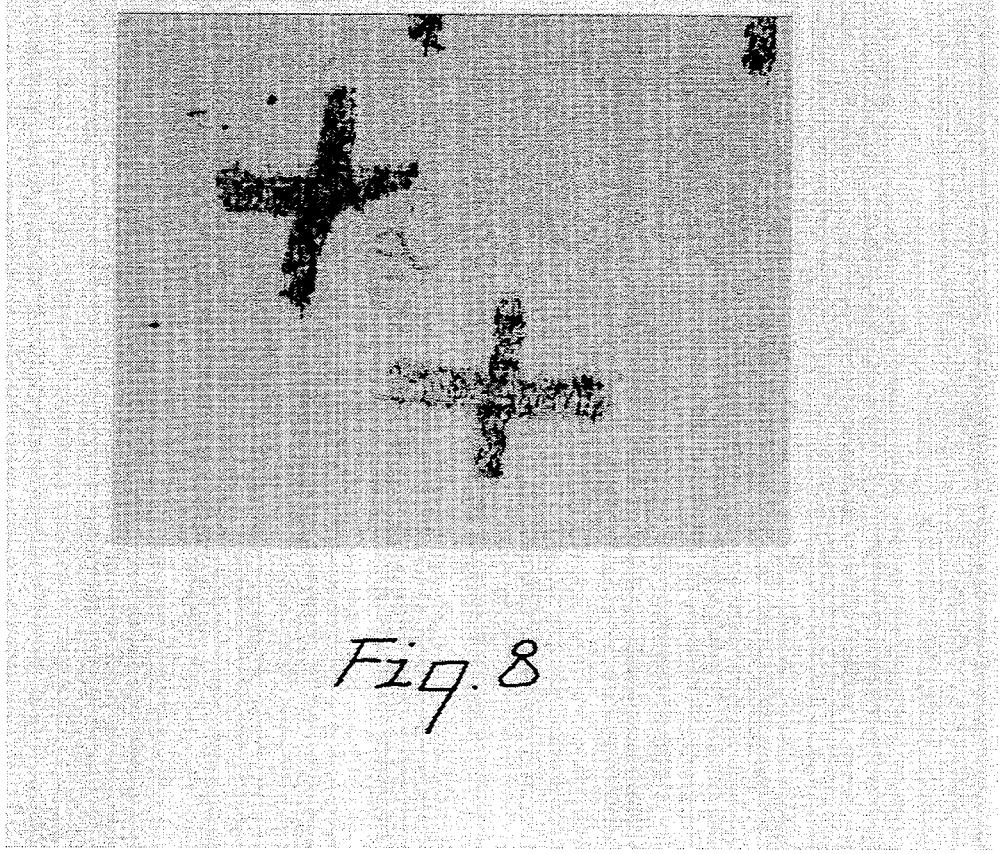
FIG. 8 is a photograph of the stretched and recovered laminate of FIG. 7 marked with the same ink.

Writability of the tape is also increased by non-adhesive coated microstructured surfaces that result when the stretched tape recovers. Either organic solvent or water-based inks will tend to flow into the microstructured surface channels and dry there. FIG. 7 shows the surface of an unstretched, untextured laminate where the ink clearly beads up. FIG. 8 demonstrates the improvement in writability for the laminate of FIG. 7, after stretching and recovery to create a microtextured surface (see example 26). The more viscous the ink, the less it will tend to wick in the microchannels of the surface and hence bleed. Similarly, the more the surface attraction between the skin layer and the ink, the better will be the writing characteristics of the microstructured surface. The writing surface characteristics of the film can also be altered with conventional additive or surface treatment techniques to the extent that they do not interfere with microtexturing.

The laminate tape backings of the present invention may be formed by any convenient layer forming process such as pressing layers together, coextruding the layers or stepwise extrusion of layers, but coextrusion is the presently preferred process. Coextrusion per se is known and is described, for example, in U.S. Pat. Nos. 3,557,265 to Chisholm et al. and 3,479,425 to Leferre et al. Tubular coextrusion or double bubble extrusion is also possible. The layers are typically coextruded through a specialized die and/or feedblock that will bring the diverse materials into contact while forming the laminate.

FIG. 1 shows a three-layer laminate tape backing construction in cross section, where the 3 is the elastomeric layer and 2 and 4 are the skin layers, which may be the same polymer or different polymers. This layer arrangement is preferably formed by a coextrusion process.

Figure 4:
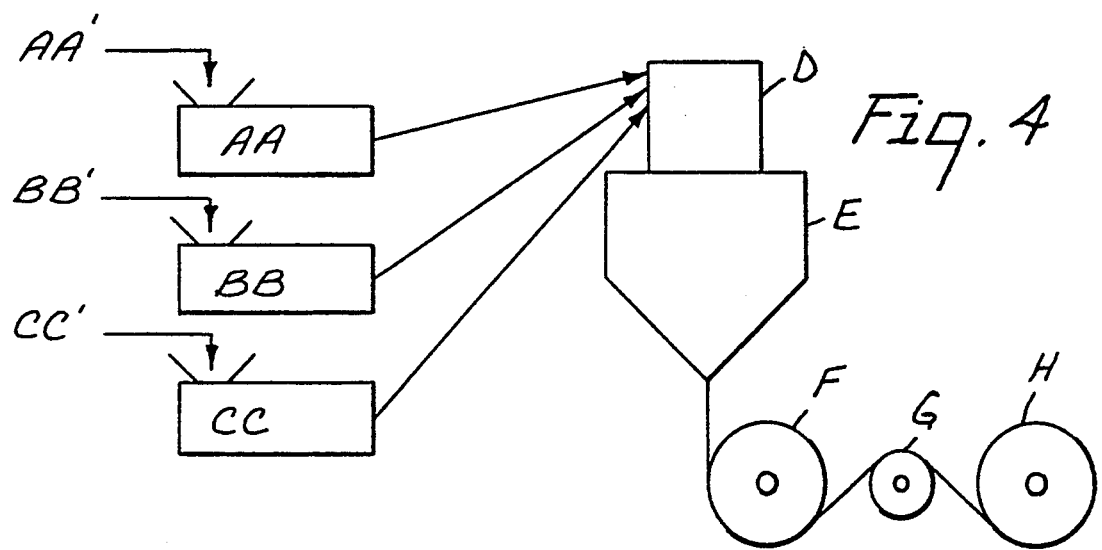
FIG. 4 is a schematic representation of a process and apparatus used to coextrude laminate tapes and/or backings.

One particularly advantageous coextrusion process is possible with special multilayer, e.g. a three-layer, combining adapters made by Cloeren Co., Orange, Tex. These adapters are described in U.S. Pat. No. 4,152,387 (Cloeren), which is incorporated herein by reference. Streams of thermoplastic materials flowing out of extruders at different viscosities are separately introduced into the adapter, containing back pressure cavities and flow restriction channels, and the several layers exiting the flow restriction channels converge into a melt laminate. The combining adapter is used in conjunction with extruders supplying the thermoplastic materials to be laminated. Such a scheme for producing the present invention is shown schematically in FIG. 4, for a three layer adapter. AA, BB, and CC are extruders. AA', BB' and CC' are streams of thermoplastic materials flowing into the feedblock or manifold die. D is the 3 or more (e.g., 5-layer) layer feedblock. E is the die, F is a heated casting roll, and G and H are rolls to facilitate take-off and roll-up of the laminate.

The die and feedblock used are typically heated to facilitate polymer flow and layer adhesion. The temperature of the die depends upon the polymers employed and the subsequent treatment steps, if any. Generally, the temperature of the die is not critical but temperatures are generally in the range of 350° to 550° F. (176.7° to 287.8° C.) with the polymers exemplified.

Whether the laminate backing is prepared by coating, lamination, sequential extrusion, coextrusion or a combination thereof, the laminate formed and its layers will preferably have substantially uniform thicknesses across the laminate backing. Preferably the layers are coextensive across the width and length of the laminate. With such a construction the microtexturing is substantially uniform over the elastomeric laminate surface. Laminates prepared in this manner have generally uniform elastomeric properties with a minimum of edge effects such as curl, modulus change, fraying and the like. Further, when wound as in a roll of tape, this will minimize formation of hard bands, winding problems, roll telescoping or the like.

The laminate backing of the invention has an unlimited range of potential widths, the width limited solely by the fabricating machinery width limitations. This allows fabrication of microtextured elastomeric tapes for a wide variety of potential uses.

After formation, the laminate tape backing can be stretched past the elastic limit of the skin, which deforms. The laminate tape backing then is recovered instantaneously, with time or by the application of heat, as discussed above. For heat recovery, the temperature of activation is determined by the materials used to form the laminate in the first instance. For any particular laminate, the activation temperature, either $T_{a-50}$ or $T_{a-90}$, can be adjusted by varying the skin/core ratio of the laminate, adjusting the percent stretch or the overall laminate thickness. The activation temperature used for a heat shrink laminate is generally at least 80° F. (26.7° C.), preferably at least 90° F. (32.2° C.) and most preferably over 100° F. (37.8° C.). When heat-activated, the stretched laminates are quenched on a cooling roller, which prevents the heat generated from the elongation from activating laminate recovery. The chill roll is below the activation temperature.

Figure 2:
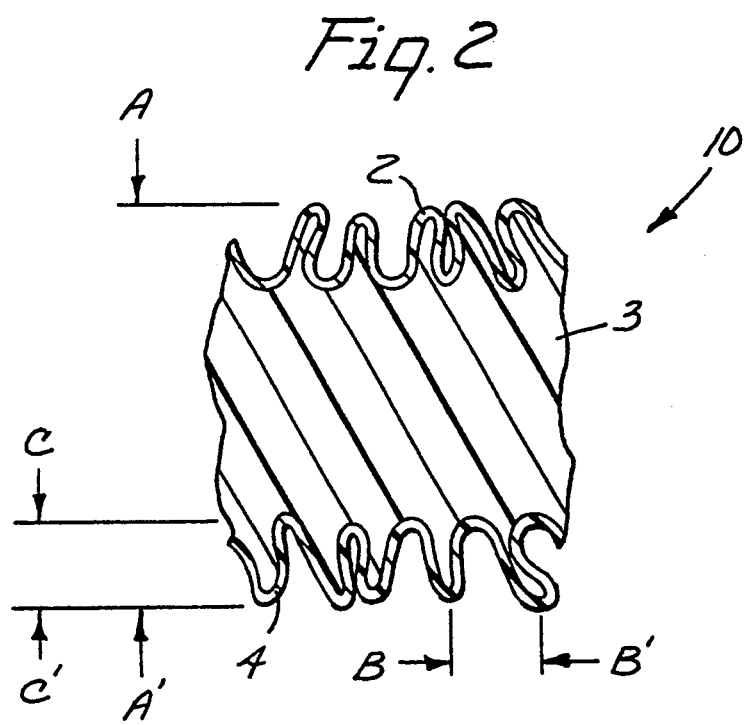
FIG. 2 is a cross-sectional segment of the FIG. 1 laminate tape backing with microstructuring caused by uniaxial stretching.

FIG. 2 is a schematic diagram of the common dimensions which are variable for uniaxially stretched and recovered laminate tape backings. The general texture is a series of regular repeating folds. These variables are the total height A-A', the peak to peak distance B-B' and the peak to valley distance C-C'. These variables were measured for a series of polyolefin/styrene-isoprene-styrene/polyolefin laminates. General ranges for A-A', B-B' and C-C' were noted. For total height (A-A'), the range measured was from 0.79 to 32 mils (0.02 to 0.81 mm). For peak-to-peak distance (B-B'), or the fold period, the measured range was from 0.79 to 11.8 mils (0.02 to 0.30 mm). For peak-to-valley distance (C-C'), the measured range was from 0.04 to 19.7 mils (0.001 to 0.5 mm). These ranges are only exemplary of the surface characteristics obtainable by the practice of the present invention. Laminate tape backings of other compositions will demonstrate different microstructures and microstructure dimensions. It is also possible to obtain dimensions outside the above ranges by suitable selection of core/skin ratios, thicknesses, stretch ratios and layer compositions.

A further unique feature of the invention laminate tape backing is depicted in FIG. 2. That is, when the material is stretched and recovered uniaxially, regular, periodic folds are generally formed. That is, for any given transverse section the distance between adjacent peaks or adjacent valleys is relatively constant.

Figure 3:
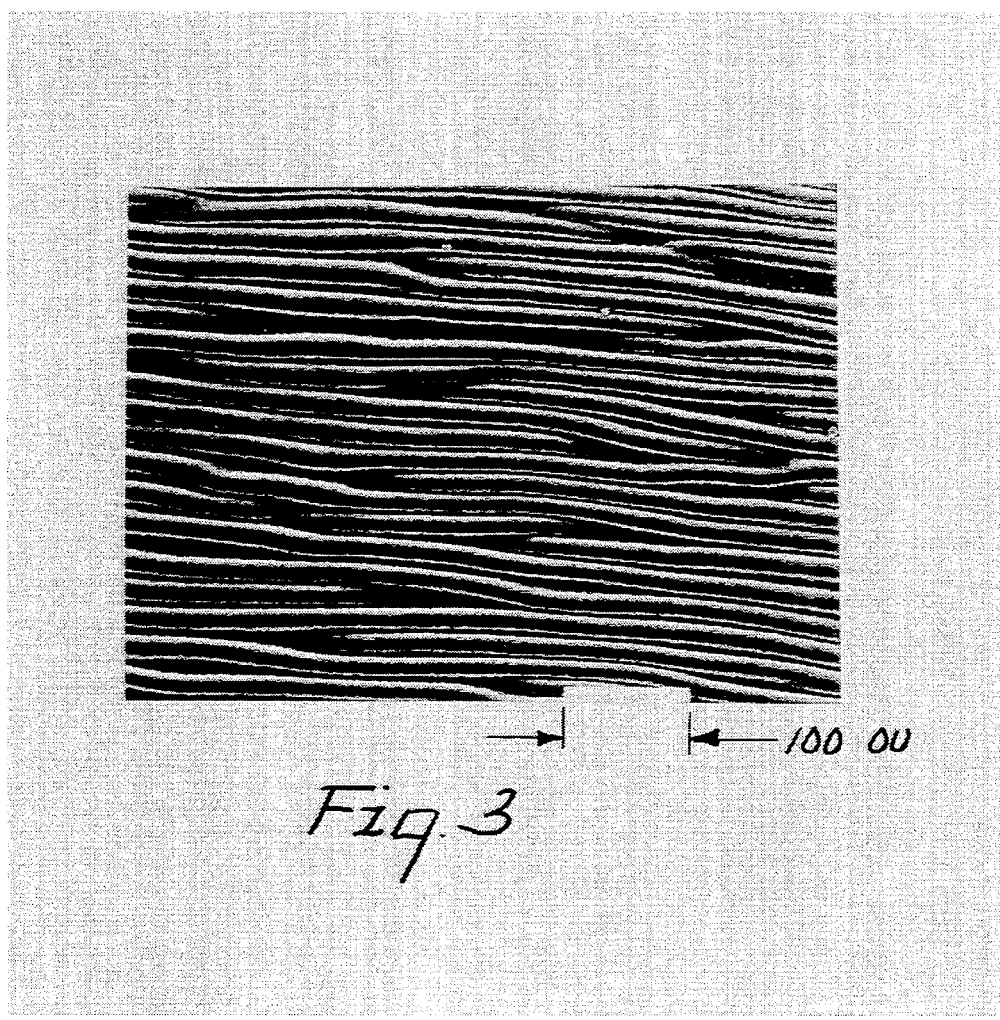
FIG. 3 is a scanning electron micrograph (200×) of a microstructured laminate tape backing that has been uniaxially stretched.

FIG. 3 shows a scanning electron micrograph of the surface of a polybutylene/styrene-isoprene-styrene (SIS)/polybutylene laminate backing of Example 6 which has been stretched past the elastic limit of the outer skin layers in the longitudinal direction and allowed to recover to form a microstructured surface. The microstructured surface corresponds to that shown schematically in FIG. 2.

The microstructured surface consists of relatively systematic irregularities whether stretched uniaxially, as was the FIG. 3 laminate tape backing, or biaxially. These irregularities increase the opacity of the surface layers of the laminate, but generally do not result in cracks or openings in the surface layer when the layer is examined under a scanning electron microscope.

Microtexturing also affects the properties of the formed tape. Uniaxial stretching will activate the tape to be elastic in the direction of stretch. Biaxial stretching will create unique surfaces while creating a laminate tape which will stretch in a multitude of directions and retain its soft feel if there is a microtextured skin backside.

It has also been found that the fold period of the microstructured surface is dependent on the core/skin ratio, as shown in Example 3. The periodicity is also indicative of the texture of the surfaces per Table II. This is again another indication of the control possible by careful choice of the parameters of the present invention.

It has also been found that the manner in which the laminate tape or backing is stretched effects a marked difference in the texture of the microstructured surface. For example, the extruded multi-layer laminate tape or backing can be stretched uniaxially, sequentially biaxially, or simultaneously biaxially, with each method giving a unique surface texture and distinct elastomeric properties. When the film is stretched uniaxially, the folds are microscopically fine ridges, as per FIG. 3, with the ridges oriented transversely to the stretch direction.

Figure 6:
FIG. 6 shows an electron micrograph (1000×) of a sample of the present invention with a polyethylene skin which was simultaneously biaxially stretched.
Figure 10:
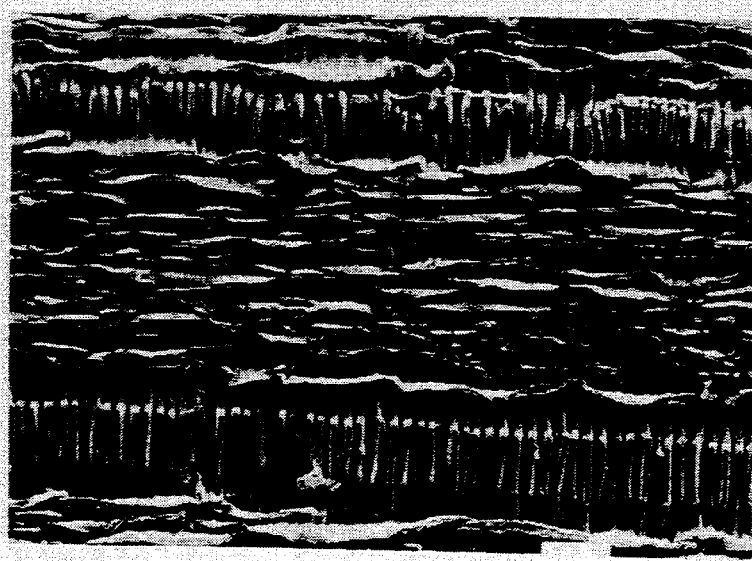
FIG. 10 is a scanning electron micrograph (100×) of the surface of a laminate tape backing which has been sequentially biaxially stretched.
Figure 11:
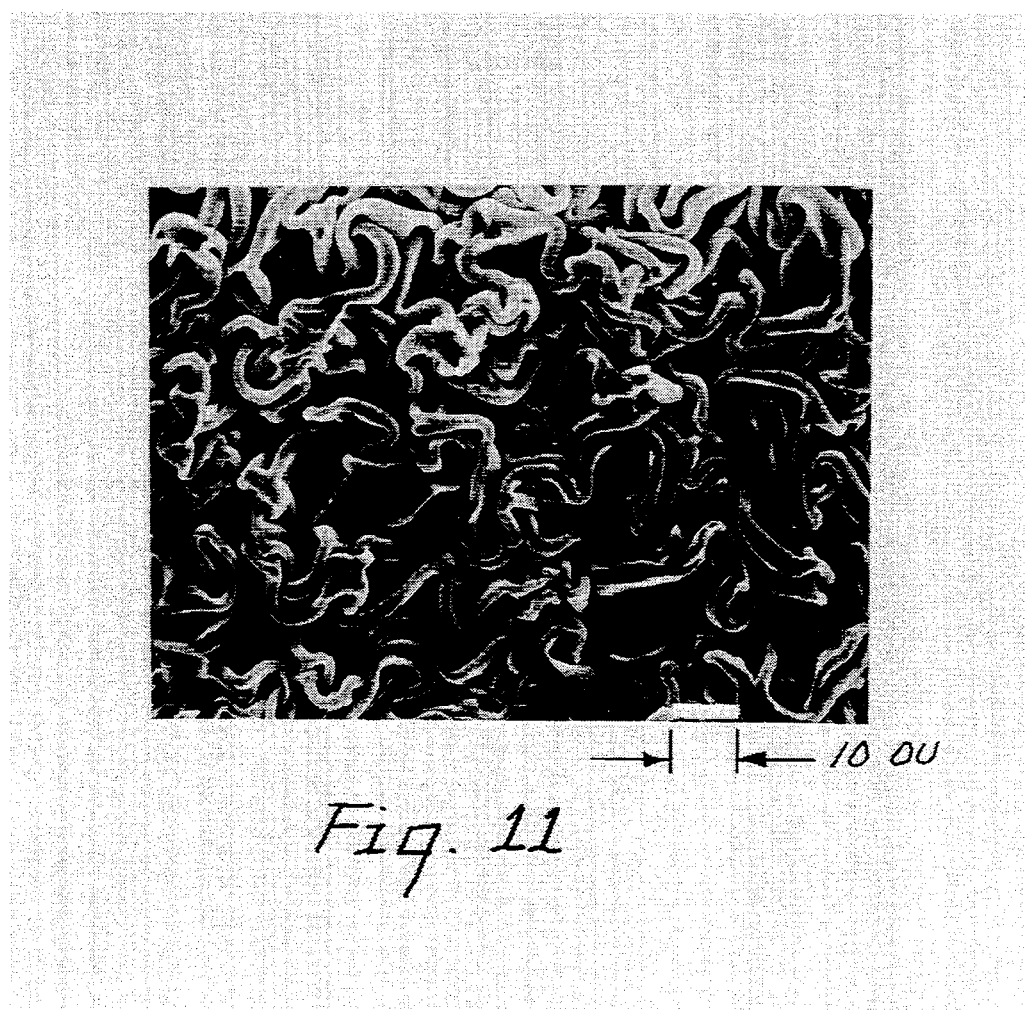
FIG. 11 is a scanning electron micrograph (100×) of a simultaneously biaxially stretched invention laminate which has a polypropylene(PP) skin.

When the laminate tape backing is stretched first in one direction and then in a cross direction, the folds formed on the first stretch become buckled folds and can appear worm-like in character with interspersed cross folds as in FIG. 10. FIG. 10 is a laminate of PP/SIS/PP with a core/skin ratio of 18 (Example 24). Other textures are also possible to provide various folded or wrinkled variations of the basic regular fold. When the film is stretched in both directions at the same time, the texture appears as folds with length directions that are random, as shown in FIG. 6 (a laminate prepared as per Example 19A with skin/core/skin thicknesses of 5/115/5 microns respectively) or FIG. 11 (Example 24). Using any of the above methods of stretching, the surface structure is also dependent, as stated before, upon the materials used, the thickness of the layers, the ratio of the layer thicknesses and the stretch ratio.

The unique continuous microstructured surfaces of the invention can be altered and controlled by the proper choice of materials and processing parameters. Differences in the material properties of the layers can change the resulting microtextured skin, but it has been found that by the careful choice of the layer ratios, total laminate film thickness, the number of layers, stretch degree, and stretch direction(s) it is possible to exercise significant control over the microstructure of the laminate skin layer.

The degree of microtexturing of elastomeric laminate backings prepared in accordance with the invention can also be described in terms of increase in skin surface area. Where the laminate shows heavy textures, the surface area will increase significantly. This is demonstrated for LLDPE/SIS/LLDPE(linear low density polyethylene) laminates in Table VIII, Example 16. In this example, as the stretch ratio increases so does the percent increase in surface area, from the unstretched to the stretched and recovered laminate; from 280 at a stretch ratio of 5, to 530 at a stretch ratio of 12. Generally the microtexturing will increase the surface area by at least 50%, preferably by at least 100% and most preferably by at least 250%. The increase in surface area directly contributes to the overall texture and feel of the laminate surface.

Increased opacity of the skin and hence the laminate backing also results from the microtexturing. Generally, the microtexturing will increase the opacity value of a clear film to at least 20%, preferably to at least 30%. This increase in opacity is dependent on the texturing of the laminate with coarse textures increasing the opacity less than fine textures. The opacity increase is also reversible to the extent that when restretched, the laminate will clear again.

It is also possible to have more than one elastomeric core member with suitable skins and/or tie layer(s) in between. Such multilayer embodiments can be used to alter the elastomeric and surface characteristics of the laminate.

Adhesive can be applied to the laminate backing by any conventional method, such as: solvent coating, by methods such as reverse roll, knife-over-roll, gravure wire wound rod, floating knife, or air knife; hot melt coating such as by slot orifice coaters, roll coaters, or extrusion coaters; and direct coextrusion during laminate formation. The adhesive will generally be applied to the as cast laminate backing or when the laminate is stretched prior to recovery. Adhesives will preferably be applied to or with the cast laminate unless it is an adhesive which does not stretch to the extent that the laminate is stretched. Although adhesive can be applied to a microstructured surface, this is not as desirable in terms of adhesive layer uniformity, ease of application or adhesive bonding to the laminate. For most applications, the adhesive will be applied continuously across the laminate backing. This eases application and collection, e.g. as a roll, and facilitates use. Adhesive can also be applied to both faces of the laminate backing.

A unique advantage of a microstructured surface formed after the adhesive is applied is the ability to improve bonding of the adhesive layer to the tape backing. It has been found that when the adhesive layer is in full contact with a microstructured surface there appears to be a mechanical priming that reduces adhesive transfer or cohesive failures in the adhesive layer. This highly advantageous feature is noted at even significantly higher peel forces than the forces which cause these problems in corresponding tapes without microstructured surfaces and with the same adhesives.

The skin layer-to-core layer contact in the stretched and activated film has been observed to vary depending on the skin and core compositions. With certain preferred constructions, the core and skin remain in full contact with the core material, filling the folds formed in the skin layers as shown in FIG. 2. This construction is extremely durable and not as subject to delamination, particularly when annealed following activation. A variation of this continuous contact construction is also possible where the elastomer fills the skin folds but is observed to cohesively fail under the folds. It is believed this occurs with thicker and/or more rigid skins that expose the underlying elastic to more concentrated stresses during relaxation. An entirely different skin/core adhesion mode is also possible. Namely, the core in some cases can completely retract from the skin under the folds, but remain sufficiently attached such that the skin does not delaminate (see Example 38, adhesive failure). This construction generally is not desirable as during use it is more easily subject to delamination as well as exposing the elastic core to air which may accelerate degradation of the elastomer.

The microstructured laminate tape is also highly conformable. This is an important feature as it allows the tape to be applied to a variety of surfaces, particularly to uneven surfaces or moving surfaces, and still give an adequate adhesive to substrate bond.

Figure 14:
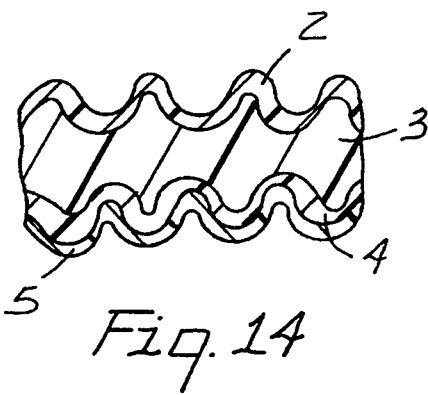
FIG. 14 is a diagram of a tape after stretch and activation where the adhesive is a thin coating.
Figure 15:
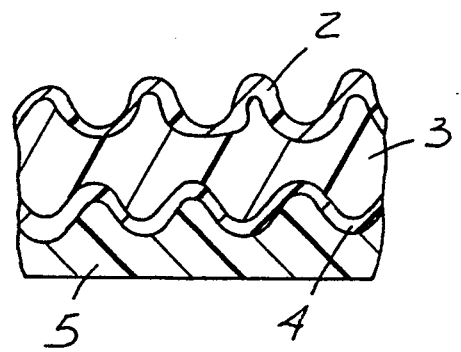
FIG. 15 is a diagram as per FIG. 14 with a thicker adhesive coating.
Figure 17:
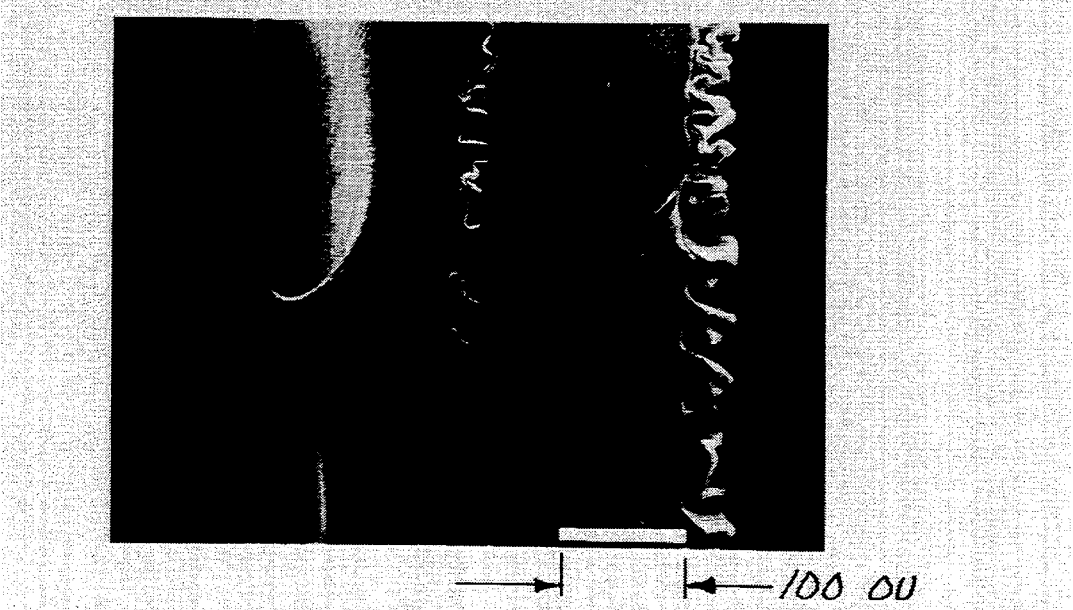
FIG. 17 is a scanning electron micrograph (200×) of a tape having a thick adhesive forming a relatively flat surface.

A further unique quality of the invention microstructured tape is its ability to exhibit a wide variation in adhesiveness to itself. The feature is particularly pronounced where both the adhesive layer and backside of the tape are microstructured. Namely, at higher rolldown pressures significantly greater levels of adhesive bonding are obtainable as compared to lower rolldown pressures. The differences in adhesive levels at differing rolldown pressures is more pronounced when a thinner adhesive is used, as shown in FIGS. 14 (where 5 is the adhesive layer) and 16, as compared to a thicker adhesive, as shown in FIGS. 15 and 17. With a thinner adhesive, the adhesive will more likely be microtextured.

It is believed that this variable self-adhesion phenomenon is related primarily to the relative amount of adhesive layer to tape backing contact area, which is potentially much higher where both the adhesive layer and the tape backside have microstructured surfaces. At low rolldown pressures, adhesive will tend to only contact the microstructure peaks on the backing. This low-contact area will be exaggerated if the adhesive layer itself has a peak and valley configuration. At higher rolldown pressures, the adhesive, microtextured or not, will have a tendency to be forced into the valleys of the backsize microstructure. This will tend to substantially increase adhesive/backside surface contact and even permit mechanical adhesive priming to the backsize in some circumstances (e.g., where the adhesive is flowable), which also increases adhesion. With softer, more flowable, adhesives the amount of pressure needed to increase adhesive levels will generally be lower. The degree and type of microstructuring will also be a significant factor in determination of the rolldown pressure variance in self-adhesion values (i.e., the degree to which the microstructures will tend to interlock). Multiaxially stretched laminates form more random structures that may interlock better than uniaxially stretched laminates. Placement orientation of the adhesive to the tape backsize also plays a significant role in the observed self-adhesion levels. The variation in self-adhesive levels obtainable due to the microstructured surface formed, on either the backsize or the adhesive face, will be quite wide due to the great variability in surface structures that one can create in the laminate skin layers, as discussed above.

Adhesive thickness will also play a significant roll in the observed variance of self-adhesion. Thicker adhesives will result in less or no self-adhesion variance due to any surface structure on the adhesive layer face. However, thicker adhesive layers will tend to flow more into a backside microstructure, which is a function of adhesive viscosity.

Thicknesses for thinner adhesives layers capable of forming a surface microstructure will be dependent on the particular microstructure formed. For example, for structures, such as those of FIG. 2, with folds having larger peak-to-valley distances and/or greater peak-to-peak distances will be capable of forming adhesive surface structures with thicker adhesive layers. Further, the relative modulus values for the particular adhesive will be a factor. Generally, an adhesive layer less than 30 microns and preferable less than 20 microns thick should be sufficient to form a definite surface structure.

Microstructured adhesive layers will have lower peel values, to any substrate, than corresponding flat adhesive layers at moderate application pressures. Again, this is due to lower contact between the adhesive and the substrate. This can result in peel values within the range acceptable for a repositionable adhesive formulation, such as those disclosed is U.S. Pat. No. 3,691,140 (Silver) and discussed in U.S. Pat. No. 4,684,685 (Shuman et al.). Generally, a 180° peel adhesion from glass of less than 8 N/25 mm, preferably less than 6 N/25 mm is characteristic of a good repositionable adhesive formulation usable with most substrates. For removable labels, a 180° peel from from glass of 2.5–6.0 N/25 mm is most preferred. For tapes cleanly removable from more delicate substrates, such as newsprint, a 180° peel from glass of 0.5 to 2.5 N/25 mm is most preferred. With the invention adhesive tapes, peel values within these ranges are obtainable by varying the adhesive layer thickness and the microstructure of the skin layer(s). By varying these factors, one is able to vary the amount or peak area of the adhesive layer available for contact with a substrate. This will affect repositionability as discussed in U.S. Pat. No. 3,857,731 (Merrill et al.). As peel values are dependent on this available adhesive contact area, other factors which can affect contact area will also influence the repositionable character of the microstructured adhesive. For example, the deformability of the skin layers will affect the amount of peak adhesive surface able to contact a substrate, as more deformable (e.g., softer skin material) fold structures will tend to more easily flatten when subjected to higher application pressures.

For some tapes, a microstructured adhesive layer and/or a nonadhesive coated microstructured backsize can function as a mechanical low adhesion backsize. For some tapes wound as a roll, this characteristic would be dependent on wind-up tension. A tape could thus be wound at a low windup tension and be readily removed by the user without the need of a chemical backsize coating. The same tape could then be applied by the user at a higher pressure and exhibit significantly higher self-adhesion values. This is an advantage over conventional backsizes which do not allow such wide adhesive level variability. Conventional backsized tapes exhibit relatively low self-adhesion regardless of the rolldown pressure. High self-adhesion is a significant advantage for tapes which are wound over themselves when used, such as insulating tape, medical tape, or the like, as discussed in U.S. Pat. No. 3,379,562. However, high self-adhesion is incompatible with forming the tape as a roll which is able to unwind.

Even activated tapes with high levels of adhesion (e.g., at zero peel angles) to a particular substrate can be removed. The high level of extensibility available with most invention tape constructions optionally coupled with the variability in adhesiveness caused by the microstructuring allows tapes with otherwise permanent adhesive peel levels to be removed. When stretched the tapes will tend to incrementally release at the leading edge of tape contact where the tape is being incrementally stretched. This leading edge release zone will travel incrementally down the tape until it is released from its substrate.

Many constructions of the invention adhesive tape can also be used as tamper indicating sealing tapes, which will indicate tampering due to the ability of the tape to change form. For example, as cast unactivated laminate tape can indicate tampering by at least three mechanisms. First, it can stretch and indicate tampering by, e.g., a change in opacity. Second, for tapes which have low adhesion between the skin and core layers, stretching will cause the layers to delaminate, again indicating tampering. Third, cast laminates can be formed which have relatively thick and/or rigid skins which will cause the laminate to tear or break up the skin. Thinner tape backings will tend to more easily stretch and indicate tampering by the first mechanism. The actual caliper required for a particular tamper indicating application will depend on the force necessary to remove or tamper with the tape on the particular package. Generally, the thinner the overall laminate tape thickness, the more sensitive it will be to tampering by any of the above three mechanisms. Even the activated tape can be tamper indicating in some instances, as when it is stretched, it will change its opacity value. This change in optical properties can also be taken advantage of by coloring the backing layers different colors. The change in skin morphology and possibly skin/core contact mechanism can change the additive effect of the multicolored layers. Further, with certain activated tapes, low adhesion between the skin and core can be used to indicate tampering by delamination. For example, the peel force of tape removal for some tape constructions will cause the skin layer to delaminate.

With certain constructions, the microtextured skin layers may tend to delaminate and/or the underlying elastomer may tend to degrade over time. This tendency is particularly problematic with ABA block copolymers. Residual stress created during the stretching and recovery steps of activating the material to its elastomeric form can accelerate this process significantly. For those constructions prone to such degradation or delamination, a brief relaxing or annealing treatment following activation may be desirable. The annealing would generally be above the glass transition point temperature ($T_g$) of the elastomer, above the B block $T_g$ for ABA block copolymers, but below the skin polymer melting point. A lower annealing temperature is generally sufficient. The annealing will generally be for longer than 0.1 seconds, depending on the annealing temperature. With commercial ABA block copolymers (e.g., Kraton TM 1107), an annealing or relaxing temperature of about 75° C. is found to be sufficient.

The laminate tape formed in accordance with the above description of the invention will find numerous uses due to the highly desirable properties obtainable. For example, the microtexture gives the elastomeric laminate tape backing a soft and silky feel. The tape can further be non-necking. This renders the elastomeric laminate tape particularly well suited for a variety of commercially important uses as an elasticizing element particularly in the garment area, where elastic webs are used in areas to engage or encircle a body portion alone or as part of a garment. Examples of such garments include disposable diapers, adult incontinence garments, shower caps, surgical gowns, hats and booties, disposable pajamas, athletic wraps, clean room garments, head bands for caps or visors or the like, ankle bands (e.g., pant cuff protectors), wrist bands, and the like.

Removability characteristics of the tape make it useful as temporary tape, removable label stock, temporary note pads or the like. With labels, it is often useful to provide a non-adhesive coated strip to permit gripping the label for removal. Writability improvements from microtexturing also make the activated laminate tape well suited for label stock and the like.

The laminate tape can be extensively used in disposable diapers, for example, as a waistband, located in either the front or side portions of the diaper at waist level, as leg elastic, as a soft outer cover sheet or in adjustable slip-on diapers, where the elastomeric laminate could be used as, or in, side panels around the hip that create a tight fitting garment or as a fastening tab. The laminate tapes can be applied as continuous or intermittent lengths by conventional methods. When applied, a particular advantage of the laminate tape is the ability to use thin elastomers with high stretch ratios. This creates a great deal of gathering or shirr when applied to the garment when stretched, which gives the shirred portion a cushion-like feel.

Garments often are shirred to give a snug fit. This shirring can be easily obtained by applying the laminate while in an unstable stretched condition and then affecting the shirr by application of heat. The elastomeric laminate can be adhered to the garment by ultrasonic welding, heat sealing and adhesives by conventional methods.

The controlled relaxation obtainable by adjusting the layer ratios, stretch ratio and direction, and layer composition makes the elastomeric tape of the invention well suited to high speed production processes where heat activated recovery can be controlled easily by hot fluids such as hot air, microwaves, UV radiation, gamma rays, friction generated heat and infrared radiation. With microwaves, additives, such as nickle powder, aluminum flakes and iron whiskers, may be needed to ensure softening of the skin to effect skin controlled recovery.

Figure 5:
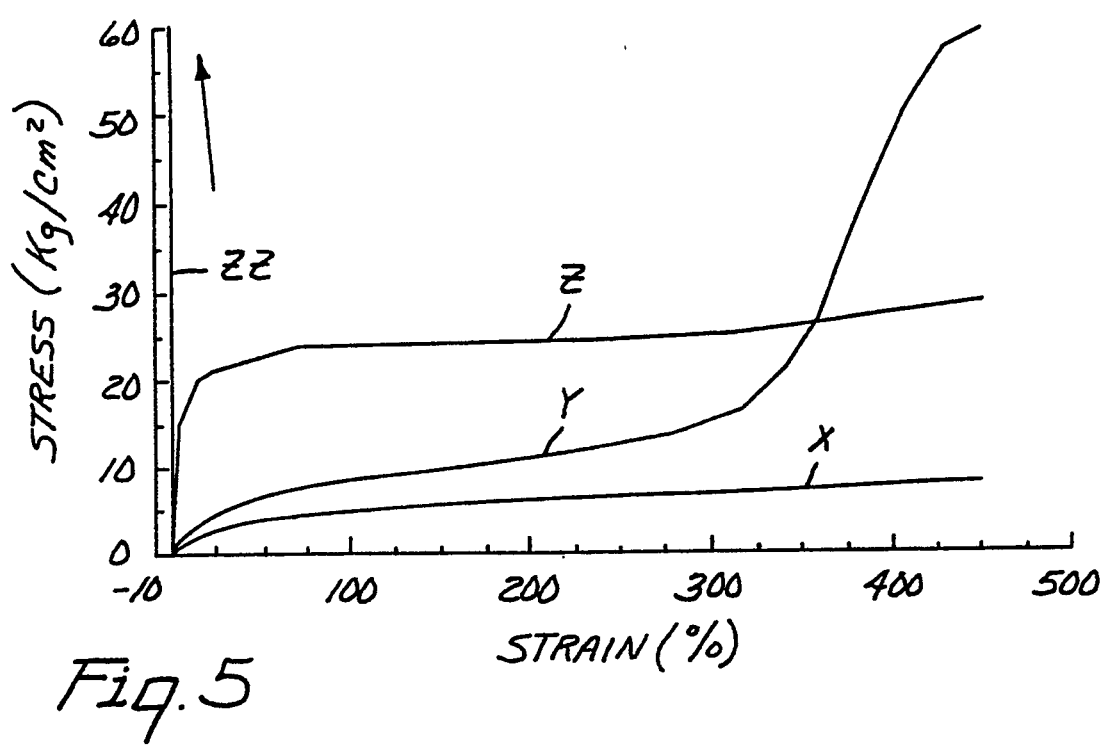
FIG. 5 is a diagram showing the stress-strain characteristics of a laminate backing and its component layers.

The counter-balancing of the elastic modulus of the elastomeric layer and the deformation resistance of the skin layer also modifies the stress-strain characteristics of the laminate tape. This also can be modified to provide greater wearer comfort when the laminate tape is used in a garment. For example, a relatively constant stress-strain curve can be achieved. This relatively constant stress-strain curve can also be designed to exhibit a sharp increase in modulus at a predetermined stretch percent, i.e., the point at which the skin was permanently deformed when activated as shown in FIG. 5, line Y. Prior to activation, the laminate is relatively rigid, line Z of FIG. 5, i.e., having a high modulus imparted due to the skin layer. The non-activated or non-stretched laminate is easier to handle and much better suited to high speed production processes than would be a conventional elastic. To achieve these benefits, the skin can be either an inner layer, an outer layer or both. In FIG. 5, line ZZ is the skin alone and line X is the elastomeric layer alone.

The elastomeric laminate tape is well suited for use as a repositionable tape, wrapping tape, insulating tape, label stock or general purpose tape. The heat shrink character of the tape can also render it suitable for heat shrink applications, particularly in view of the conformable nature of the tape. The tape has the advantage of the ability to form a natural LAB, ink receptivity, mechanical adhesive priming and variable adhesive levels.

The elastomeric laminate tape will also easily electrostatically charge when rubbed. This ability, coupled with the enclosed spaces, makes sheets of the microstructured laminate tapes useful as dust wipes, or as dust mats (e.g., in a clean room). Further, the polymer skin will often attract and store oils. The tapes could be formed into a multitude of stacked sheets, and as they are removable, could be removed when used to expose an underlying clean sheet.

The following Examples are provided to illustrate presently contemplated preferred embodiments and the best mode for practicing the invention, but are not intended to be limiting thereof.

Examples 1–32 are illustrations of laminates suitable for use as backings for the invention adhesive tapes.

EXAMPLE 1

A five-layer laminate was prepared from two outer layers of 5.08 cm by 5.08 cm, 2000 molecular weight polystyrene and two layers of 5.08 cm by 5.08 cm of 2 mil (0.0508 mm) thick linear low density polyethylene (LLDPE) film (Dow TM 61800, Dow Chemical Corp., Midland, Mich.) and a core layer of 5.08 cm by 5.08 cm of 125 mil (3,175 mm) thick styrene-isoprene-styrene (SIS) film (Kraton TM 1107, available from Shell Chemical Company, Belpre, Ohio) by heating at 160° C. under 2000 pounds per square inch (140 kilograms per square cm) of a flat press. The resulting film laminate was about 5 mil (0.127 mm) thick. The polystyrene layers were a processing aid to help form a uniform layered film. The thin brittle polystyrene layers of the laminate were peeled away, and a clear film remained. After stretching the clear film by hand to 500%, and allowing it to recover, a smooth and pleasing surface was observed with the naked eye, and surprisingly, examination under a microscope disclosed a continuous, deeply textured, microstructured surface. Since this sample was uniaxially stretched, fine ridges were observed, oriented transversely to the stretch direction, said ridges having a height to width ratio of about 2 to 1.

EXAMPLE 2

A continuous coextrusion was carried out to prepare a three-layer laminate with two outer skin layers of LLDPE and a core layer of SIS using polymers as described in Example 1. Three laminates of 8.5, 4.7, and 3 mil (215, 120 and 78 microns) thickness were prepared using a Rheotec ™ (Rheotec Extruder Co., Verona, N.J.) extruder to feed the SIS layer from a tee union into the center of a cross union and a Berlyn ™ (Berlyn Corp., Worchester, Mass.) extruder was used to feed the two LLDPE layers into the two opposite sides of the cross union and then the three laminated layers of film were drawn from the 425° F. (218° C.) die in widths of 18 inches (45.7 cm). The laminates had skin/core skin thicknesses in microns of 20/175/20, 16/90/14 and 10/60/8, respectively, determined under a light microscope. After the film was stretched past the elastic limit of the outer skin layers, it deformed and demonstrated a microstructured surface upon recovery. When initially uniaxially stretched about 500%, these laminates necked down, width wise, to about 40% of their unstretched width. Upon subsequent restretching to about 500%, the films surprisingly necked down very little, as shown in Table I.

TABLE I

| Sample | % Reduction in Width Thickness upon Restretching |
|---|---|
| 78 microns | 5.2 |
| 120 microns | 3.2 |
| 215 microns | 2.8 |

The films thus essentially remained constant in width after initial stretching. Not all stretched films will show this non-necking property. The non-necking is a property of the unique unfolding of the stretched surface layers of the present invention, and is a function of the skin thickness and modulus, i.e., strength. This strength must be high enough to prevent width contraction of the core layer upon re-stretching. That is, it is a balance of skin and core forces. Very soft or very thin skinned materials, therefore, need to be thicker for the laminate to possess this property.

EXAMPLE 3

A continuous coextrusion was carried out to prepare three-layer laminates with two outer layers of polypropylene and a core elastomeric layer of a styrene-isoprene-styrene block copolymer. A 2 inch (5.1 cm) screw diameter Berlyn ™ extruder was used to feed the elastomer (Kraton ™ 1107, Shell Chemical Company, Beaupre, Ohio) and a Brabender ™ 1.25 inch(3.18 cm) screw diameter extruder (available from C. W. Brabender Instruments, Inc., N.J.) was used to feed the two polypropylene (Escorene ™ 3085, available from Exxon Corporation, Houston, Tex.) layers into the Cloeren ™ (Cloeren Co., Orange, Tex.) feedblock, and were extruded through a single manifold 18 inch(46 cm) wide film die. The film was cast onto a 60° F.(16° C.) cast roll at 14.7 ft/min(509 cm/min) at varying total caliper as described in Table II. Films of varying outer layer thickness were prepared.

The films were tested for relaxation by initially uniaxially stretching each sample by hand to just short of its breaking point, which was generally about 650%, releasing the sample, and observing any recovery. Recovery after initial draw was then categorized as instantaneous recovery (I), slow recovery with time (T), heat required for recovery (H) and permanent deformation (P), i.e. no significant recovery. Results are shown in the following table.

TABLE II

| SAMPLE NO. | TOTAL SKIN THICKNESS (microns) | CORE THICKNESS (microns) | CORE THICKNESS SKIN THICKNESS | RECOVERY | TEXTURE OF LAMINATE |
|---|---|---|---|---|---|
| A | 5 | 90 | 18 | I | F |
| B | 8 | 145 | 18 | I | F |
| C | 12 | 175 | 14.6 | I | M |
| D | 7 | 54 | 7.7 | I | F |
| E | 14 | 100 | 7.1 | T | C |
| F | 8 | 48 | 6 | T-H | F |
| G | 20 | 45 | 2.25 | P | Smooth |

| Sample No. | % Change in Width upon Restretching sample | C.O.F. | Periodicity |
|---|---|---|---|
| A | 1.4 | — | |
| B | 2.8 | 0.59 | 10μ |
| C | 2.0 | 0.67 | 45μ |
| D | 2.0 | | |
| E | 0 | 0.75 | 90μ |
| F | 0 | | |
| G | Did not recover | | |

The texture of the laminate is evaluated both visually and by touch after recovery and classified as fine (F), medium (M), coarse (C) or smooth (no texture discerned). The texture was also measured objectively in samples B, C and E by the periodicity (distance between folds) of the samples. It was noted that as the regular folds get coarser, they also appear larger and more widely spaced. Although the large folds are more subject to having more random peak-to-peak distances, they are still quite regularly spaced.

The samples were also tested for necking characteristics expressed as % change in width upon restretching of the sample. Although necking was not significant for any of these samples, generally, as skin thickness fell and the core-to-skin thickness ratio rose, necking increased.

Periodicity and C.O.F. are also shown for samples B, C and D which are both inversely related to the core/skin thickness ratio. The original C.O.F. for the samples was over 3.8, thus the microtexturing produced a significant overall reduction of C.O.F.

EXAMPLE 4

A multilayer laminate was prepared by laminating cast laminates of polypropylene/Kraton TM 1107/polypropylene prepared as in the previous example. The total thickness of each cast laminate was 2.8 mil (0.062 mm). The core/skin ratio was 12:1. The laminated laminate was formed of 6 cast laminates in a hot press at 200° C. at 140 kilograms per square centimeter pressure for five minutes. The formed film was then cooled in a 21° C. water bath. The resulting laminate was 6 mil(0.15 mm) thick and appeared like the cast film but thicker. After stretching approximately 300% and instantaneous recovery, the film displayed a coarse microtextured skin and microtextured inner skin layers.

EXAMPLE 5

A continuous coextrusion was carried out to prepare three-layer laminates with two outer layers of a 70/30 by weight blend of poly(vinylidene fluoride) (Solef TM 1012, Solvay Co., France) and poly(methyl methacrylate) (VO44, Rohm and Haas Corp., Bristol Pa.) and a core layer of Kraton TM 1107. A 2 inch(5.1 cm) diameter Berlyn TM screw extruder, at 10 RPM screw speed, was used to feed the core layer polymer and a 2 inch(5.1 cm) diameter screw Rheotec TM extruder, at 25 RPM, was used to feed the skin layer polymer blends into a Cloeren TM feedblock and the melt laminate was extruded through a single manifold die, 18 inches(46 cm) wide (Extrusion Dies, Inc., Chippawa Falls, Wis.), at 420° to 450° F.(215° to 232° C.) onto a 78° F.(26° C.) cast roll at 17.0 or 15.3 revolutions per minute (RPM), respectively. The film laminate thicknesses obtained were 5.5 and 6.0 mil (0.14 and 0.15 mm) with core/skin ratios of 6:1 and 7.5:1, respectively.

Both laminates were stretched 400% and allowed to immediately recover. In each case, a laminate with a fine glossy microtextured surface was obtained.

EXAMPLE 6

A continuous coextrusion was carried out to prepare two distinct three-layer laminates with two outer layers of a 50/50 blend of two polybutylene resins, Shell TM 0200 and Shell TM 0400, and a core elastomeric layer of Kraton TM 1107. A 2 inch(95.2 cm) diameter screw Berlyn TM extruder was used to feed the Kraton TM 1107 at a screw speed of 10 RPM. A 1.25 inch(3.18 cm) diameter Brabender TM screw extruder was used to feed the two polybutylene blend layers at screw speeds of 10 and 12 RPM into a Cloeren TM feed block. The laminates were extruded through a single manifold 18 inch(46 cm) wide film die at 430° F.(221° C.) onto a 60° F.(16° C.) cast roll at either 8.8 or 7.6 ft/min(2.7 or 2.3 m/min), maintaining a total caliper of 0.003 inches(0.076 mm) for both samples. This produced two films of varying outer skin thicknesses with the same total laminate thickness. The core/skin ratios were 13:1 and 5:1, respectively.

Also, the same equipment was run at a Brabender TM extruder speed of 35 RPM and a cast roll speed of 8.6 ft/min(2.6 m/min), all other conditions the same as above, to give a 0.005 in(0.127 mm) thick laminate (comparative) with thick overall skin layers, and a core/skin ratio of 2.6:1.

The texture for each sample was noted after each laminate was stretched by hand just short of its breaking point, about 4:1, and allowed to recover, the first two runs instantly and the third (comparative) with heat. The textures were classified as very fine, fine and none. This data is shown in Table III below.

TABLE III

| Brabender TM Speed (RPM) | Cast Roll Speed (cm/min) | Total Film Thickness (cm) | Texture |
|---|---|---|---|
| 10 | 268 | 0.0081 | very fine |
| 12 | 232 | 0.0081 | fine |
| 35 | 262 | 0.013 | none |

EXAMPLE 7

A continuous coextrusion was carried out to prepare five-layer laminates with two outer layers of linear low density polyethylene, ethylene vinyl acetate tie layers of Elvax TM 260(EVA) (available from Dupont Corporation, Wilmington, Del.) and a core elastomer layer of styrene-isoprene-styrene block copolymer. A 2 inch(5.1 cm) screw diameter, 4D ratio Berlyn TM extruder was used to feed the elastomer layer (Kraton TM 1107). A Rheotec TM 2 inch(3.18 cm) screw diameter extruder was used to feed the two polyethylene layers, and a 1 inch(2.54 cm) screw diameter 3M-made extruder was used to feed the two Elvax TM layers into a Cloeren TM feedblock.

The laminates were extruded through a single manifold 18 inch(46 cm) wide film die at 375° F.(190° C.) onto a 60° F.(16° C.) cast roll at varying total caliper or thickness as described in Table IV. Films of varying layer thickness were thus prepared. This example also demonstrates how casting roll speed affects film thickness.

The EVA tie layers add bonding strength between the LLDPE outer layers and the SIS core layer, resulting in a more durable laminate than such a film without the EVA, yet does not interfere with the way the laminate behaves with respect to surface texture. This tie layer is, of course, very thin compared to the other layers.

TABLE IV

PROCESSING CONDITIONS FOR SAMPLES

| NO. | BERLYN+ RPM | RHEOTEC++ RPM | CASTING ROLL SPEED (RPM) | NIPP ROLL SPEED (RPM) | FILM THICK- NESS (microns) | SUR- FACE TEXT- URE* | 1" EXT.' RPM |
|-----|------|------|------|------|-------|------|------|
| 7A | 30 | 8 | 15 | 15 | 132.0 | F | 24 |
| 7B | 30 | 8 | 15 | 15 | 132.0 | F | 24 |
| 7C | 30 | 8 | 7 | 7 | 272.0 | MF | 20 |
| 7D | 30 | 8 | 4 | 4 | 508.0 | C | 20 |
| 7E | 30 | 8 | 14 | 14 | 124.0 | F | 20 |
| 7F | 30 | 8 | 25 | 25 | 71.0 | VF | 20 |
| 7G | 30 | 8 | 48 | 48 | 25.4 | SF | 20 |

+Berlyn ™ extruder temperature same for all samples: Zone 1 = 149° C., Z2 = 177, Z3 = 193, Z4 = 204, Z5 = 204, Z6 = 204
++Rheotec ™ extruder temperature same for all samples: Zone 1 = 110° C., Z2 = 149, Z3 = 149, Z4 = 160
'1" (2.54 cm) extruder temperature same for all runs: Zone 1 = 143° C., Z2 = 191, Z3 = 191
*F = Fine microtexture, MF = medium fine, VF = very fine, SF = super fine, C = coarse Since the extruder conditions were close to constant for all of the above runs, the core thickness to skin thickness ratio will be the same for all of the above runs, approximately 13:1 as will be the core/tie layer ratio at 30:1. Thus, it will be noted that the total film thickness column of Table IV correlates exactly with the surface texture column. The range of values goes from a total film thickness of 1.0 mil(25 microns) and a texture of super fine, to 20.0 mil(508 microns) and a texture of coarse, all from a stretch of 5:1 and an instantaneous recovery. Thus, it can be seen that the thicker materials give coarser textures and that by controlling the physical parameters, the texture can be controlled.

EXAMPLE 8

A three-layer LLDPE/SIS/LLDPE film was made as in the previous examples using a Berlyn ™ extruder with a screw speed of 20 RPM to feed the Kraton ™ 1107, and a Brabender ™ extruder with a screw speed of 17 RPM to feed the Dow Chemical 61800 linear low density polyethylene (LLDPE) to a Cloeren ™ feedblock. The laminate was extruded through a single manifold 18 inch(46 cm) wide film die onto a casting roll at 85° F.(29° C.), and a speed of 13.7 ft/min(4.18 m/min) to give a laminate with a core/skin ratio of 15.6:1 and a total thickness of 125 microns. The film was uniaxially stretched 4:1 and instantaneously recovered, the coefficient of friction of the film was measured from the stretched and recovered film, and compared to the unstretched film. The data is shown in Table V. MD denotes Machine direction and TD denotes transverse direction.

TABLE V

| Sample | Static COF | Dynamic COF |
|--------|------------|-------------|
| unstretched MD | 4.5 | 4.2 |
| unstretched TD | 4.6 | 3.7 |
| stretched MD | 0.4 | 0.3 |
| stretched TD | 0.5 | 0.5 |

This data is indicative of the large drop in the coefficient of friction for the stretched film compared to its unstretched precursor and is also indicative of the unique microtextured surface of laminates of the present invention.

EXAMPLE 9

A three-layer laminate of the present invention was made using the set-up of Example 8. The Berlyn ™ extruder, operating at a screw speed of 10 RPM, was used to feed a polyurethane (Pellethane ™ 2102-75A from Dow Chemical) core material. The Brabender ™ extruder operating at a screw speed of 7 RPM was used to feed a blend of Amoco ™ 3150B(Amoco oil Co., Chicago Ill.) high density polyethylene (HDPE) and Kraton ™ 1107 in a 95:5 ratio, as the skin material, to the Cloeren ™ feedblock. The small amount of Kraton ™ 1107 was added to the skin layer to increase the adhesion of the skin layer to the core layer. The laminate was extruded through a single manifold, 18 inch(46 cm) wide, film die onto a casting roll at a temperature of 70° F.(21° C.) and a speed of 21 ft/min(6.4 m/min) to give a 69 micron laminate with a core/skin ratio of 13.7:1. The laminate exhibited a microtextured surface after stretching 600% and instantaneous recovery.

EXAMPLE 10

A three-layer laminate of the present invention was made using the set up of Example 8. The Berlyn ™ extruder operating at a screw speed of 60 RPM was used to feed a triblock copolymer elastomer of styrene-butadiene-styrene (SBS) (Kraton ™ 1101) as a core material, and a Killion ™ (Killion Extruder Co., Cedar Grove, N.J.) extruder was used to feed a Dow ™ 3010 LLDPE material to a Cloeren ™ three layer die. The extrudate was cast upon a casting roll at a temperature of 85° F.(29° C.) and a speed of 41 ft/min(12.5 meters/minute). The resulting 5 mil(0.127 mm) thick film with a core/skin ratio of 8.9:1 was easily stretched 7.5:1 and upon instantaneous recovery a fine textured laminate was formed.

EXAMPLE 11

A three-layer laminate of the present invention was made using the set up of Example 4, with the Berlyn ™ extruder feeding a Kraton ™ G 2703 styrene-ethylene butylene-styrene (SEBS) block copolymer at a screw speed of 20 RPM, and the Brabender ™ extruder feeding an Exxon ™ PP-3014 polypropylene at a screw speed of 5 RPM, to a Cloeren ™ feedblock. This material was then extruded through a 18 inch(46 cm) film die onto a casting roll at a temperature of 34° F.(1.1° C.). The film produced was easily stretched 600% and formed a fine textured surface after it was allowed to recover instantaneously. The layer thicknesses determined under a light microscope were 15/162/12 microns skin/core/skin, respectively.

EXAMPLE 12

This example demonstrates the use of varying skin and core materials. In all runs, the line conditions were identical using a Cloeren ™ feedblock at 400° F.(204°

C.). The core extruder was the Brabender TM discussed above with temperatures in zones 1-4 of 178°, 210°, 210° and 216° C., respectively. The die was at 400° F.(204° C.) and the casting wheel at 51° F.(11° C.).

TABLE VI

| # | CORE | SKIN | CORE SKIN RATIO | % STRETCH | SHRINK-AGE | TEXTURE |
|---|------|------|-----------------|-----------|------------|---------|
| 12A | Kraton TM 1107 | ELVAX TM 360 | 9.6 | 700 | I | F |
| 12B | Kraton TM 1107 | (Polyester) (Eastabond TM FA-300) | 4.4 | 600 | I | F |

12A in Table VI demonstrates that elastomers can be used for the skin when a more elastic core is used and with appropriate stretch for a 115 micron(u) film. 12B demonstrates the use of a polyester skin in a 120 micron film. The laminate designated 12B, despite the relatively large core-to-skin ratio, was of a relatively fine texture and instant shrink recovery. This is due primarily to the low modulus of the polyester (compare to Example 3).

FA-300 is available from Eastman Cemicals Co., Kingsport, Tenn.

EXAMPLE 13

Nylon 66 (Vydyne TM 21 of the Monsanto Co., St. Louis, Mo.), the condensation product of adipic acid and hexamethylene diamine, was used as the skin in accordance with the procedure outlined in Example 8. The core was a SIS (Kraton TM 1107) block copolymer. The nylon and Kraton TM were extruded at 525° F.(274° C.) and 450° F.(232° C.), respectively into a 500° F.(260° C.) die. A 4 mil(0.1 mm) thick film was formed with a core-to-ratio of 18:1. A microtextured surface formed after a 4:1 stretch and instant recovery.

EXAMPLE 14

In order to increase the tackiness of the core and lower core layer modulus and decrease its viscosity, a solid tackifying rosin Wingtack TM (Goodyear) was blended with Kraton TM 1107 in ratios of 10/90, 20/80 and 30/70 using the arrangement of the previous example, in 91, 114 and 165 micron films, respectively. The die temperature was 380° F.(193° C.) with the Kraton TM blend fed at a rate of 18.5 pounds/hour(0.14 kg/min) and the polyethylene skin (LLDPE; Dowlex TM 2500, Dow Chemical Co., Rolling Meadows, Ill.) fed at a rate of 6 pounds/hour(2.72 kg/hr). The core-to-skin ratios were 6.2:1. For all three Kraton TM blends, a fine microtextured surface of the laminate was obtained when a 6:1 stretch was employed and gave instant shrink recovery.

EXAMPLE 15

The relationship between skin thickness and percent stretch to surface texture (measured by periodicity) was explored using a SEBS core (Kraton TM G1657) and a polypropylene skin (Exxon TM 3085). The Berlyn TM extruder was used for the core and the Rheotec TM extruder was used for the skin, fed into a Cloeren TM feedblock. A single-layer drop die was used at 420° F.(216° C.), the casting roll operated at 38.9 ft/min(11.9 m/min.) and 50° F.(10° C.). The results are shown in Table VII below.

TABLE VII

| # | AVG. SKIN THICKNESS (μ) | CORE/ SKIN RATIO | STRETCH % | PERIODICITY (μ) | SHRINK MECHANISM |
|---|---|---|---|---|---|
| 15A | 14 | 6 | 600 | 29 | I |
|  |  |  | 250 | 56 | I |
| 15B | 17.5 | 6.1 | 550 | 39 | I |
|  |  |  | 350 |  |  |
| 15C | 21 | 4.4 | 550 | 46 | H |
|  |  |  | 350 | 71 | H |
| 15D | 20 | 4.3 | 550 | 47 | H |
|  |  |  | 300 |  |  |
| 15E | 23 | 3.7 | 500 | 63 | H |
|  |  |  | 350 | 69 | H |

AS the stretch percent increased for each sample, the periodicity decreased indicative of the finer microtexturing obtained. This shows that stretch percent can be used to vary the surface structure of the laminate.

Further, as skin thickness increased, so did the periodicity. In all samples, the core thickness was approximately constant at 85μ's. Skin thickness on a constant core can thus be directly related to the surface texture obtainable. As can be seen in the above Table IV, for relatively constant stretch % as the skin thickness increased so did the periodicity. The thick skinned samples thus produced coarser textures. This can, of course, be used to manipulate the skin and hence laminate characteristics.

EXAMPLE 16

The sample tested was that prepared in Example 8 the stretch ratio was varied from 2:1 to 13:1.

TABLE VIII

| Stretch ratio | Periodicity (μ) | % Area Increase |
|---|---|---|
| 2 | (random wrinkles) |  |
| 3 | 30 |  |
| 4 | 12 |  |
| 5 | 10 | 280 |
| 6 | 8 |  |
| 7 | 7 |  |
| 8 | 6.5 | 390 |
| 9 | 6 |  |
| 10 | 5.5 |  |
| 11 | 5 |  |
| 12 | 4 | 530 |
| 13 | 3 |  |

As can be seen from Table VIII, the relationship between stretch ratio and periodicity demonstrated in Example 15 holds up for this LLDPE/SIS/LLDPE laminate. As the stretch ratio increases, the periodicity decreases first rapidly, then slowly in a substantially exponential manner. Further, the increase in area increases with an increase in stretch ratio.

EXAMPLE 17

The relationship between stretch, core/skin ratio and shrink mechanism was demonstrated using the procedure of Example 4 and Example 15 for polypropylene/Kraton TM 1657 (SEBS)/polypropylene laminates. The material was stretched at the rate of 5 cm/sec. and held for 15 seconds. The film was allowed to shrink for 20 seconds and then heat shrunk in a water bath for 5 seconds at 160° F.(71.1° C.).

The length of the film after shrink was then compared to the length of the film after the 20 second hold period and the length after stretch to determine the shrink mechanism in operation. The results of this comparison is shown in Table IX below.

TABLE IX

| CORE/SKIN RATIO | STRETCH RATIO(S) | SHRINK MECHANISM |
|---|---|---|
| 6.0 | 3.8/5.3/6.2 | I |
| 5.3 | 4.6/5.3 | S |
|  | 6.5 | I |
| 5.1 | 4.3/5.0 | H |
|  | 5.5 | S |
|  | 6.8 | I |
| 4.8 | 4.2/4.0 | H |
|  | 6.0 | T |
|  | 6.5 | F |
| 4.0 | 4.0/5.2/6.0 | H |
| 3.7 | 4.2–6.8 | H |
| 3.4 | 4.0 | N |
|  | 4.7–6.0 | H |

N = None, H = Heat, S = Slow time, T = Time, F = Fast time, I = Instant

Fast is when more than 15% recovery occurred at 5 seconds. Medium time is where greater than 15% recovery occurred at 20 seconds. Slow time is where greater than 15% recovery was not noted until 60 seconds after stretch.

EXAMPLE 18

Polypropylene (Exxon TM 3145) was added to a Kraton TM 1107 (SIS) elastomer as a modifier for the core material. The skin used was an Exxon TM 3014 polypropylene (PP). The cores prepared contained 5 and 10 percent Exxon TM 3145 polypropylene by weight. The relationship between stretch, the shrink mechanism and texture was tested. The results are in the following Table.

TABLE X

| Core/Skin Ratio = 6.9, 112 microns thick, 10% PP in Core | | | | | |
|---|---|---|---|---|---|
| % Stretch | 320 | 410 | 510 | 590 | |
| Shrink Mechanism | None | None | Heat | Heat | |
| Texture | — | — | Coarse | Coarse | |
| Core/Skin Ratio = 8.0, 125 microns thick, 10% PP in Core | | | | | |
| % Stretch | 280 | 380 | 480 | 570 | |
| Shrink Mechanism | None | None | Heat | Heat | |
| Texture | — | — | Coarse | Coarse | |
| Core/Skin Ratio = 8.8, 84 microns thick, 5% PP in Core | | | | | |
| % Stretch | 270 | 320 | 400 | 500 | 590 |
| Shrink Mechanism | Heat | Heat | Heat | Slow Time | Fast Time |
| Texture | Coarse | Coarse | Coarse | Med | Fine |

As can be seen, the addition of PP to the core decreases the shrinkability of the laminate. The polypropylene appears to reduce the elasticity of the core thereby permitting the restraining forces of the skin to more easily dominate the elastic strain imposed by the deformed elastic core.

EXAMPLE 19

Figure 9:
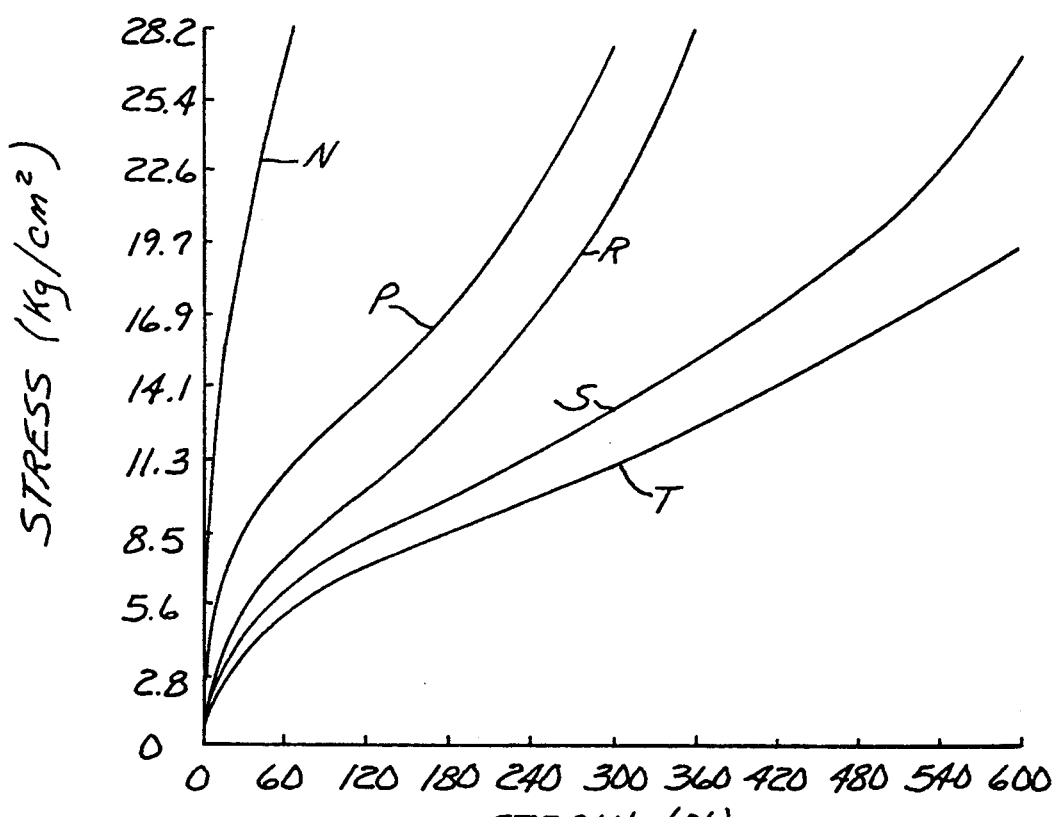
FIG. 9 (T-N) are stress/strain curves for a series of laminate films.

The effect of adding a stiffening aid, polystyrene, to an elastomeric core material was tested. The skin comprised a linear low density polyethylene (Dowlex TM 6806). The core was a blend of SIS (Kraton TM 1107) and polystyrene (500PI or 685W, both from Dow Chemical Co.). All samples were of a 3-layer construction (skin/core/skin) with a total thickness of 4.5 mil(0.11 mm) and a core/skin ratio of 8:1. All samples were then stretched 400% and instantaneously recovered. Tensile curves were then generated which demonstrated that the laminates became stiffer with increasing polystyrene content (as shown in FIG. 9 (T-N), shown also in the following Table XI.

TABLE XI

| SAMPLE # | % P.S.(Type) | 5% YOUNGS MODULUS (kg/cm$_2$) |
|---|---|---|
| 19A(T) | 0 | 11.5 |
| 19B(S) | 10 (500 PI) | 20.7 |
| 19C(R) | 30 (500 PI) | 29.4 |
| 19D(P) | 40 (685 W) | 68.6 |
| 19E(N) | 50 (685 W) | 188.4 |

EXAMPLE 20

In this example, the effect of the addition of Wingtack TM tackifier to the core elastomer was investigated. The laminate material of Example 14 was compared to a 3-layer laminate (20) comprising LLDPE/Kraton TM 1107/LLDPE. Both samples were 4 mil(0.10 mm) in total thickness with core/skin ratios of approximately 8:1. These materials were of the instant shrink type when stretched from 4:1 to 13:1.

TABLE XII

| EXAMPLE | 5% YOUNGS MODULUS |
|---|---|
| 20 (Comp) | 109 kg/sq.cm. |
| 14 | 47.9 kg/sq.cm. |

As can be seen from Table XII, the use of a viscosity reducing aid/tackifier has the opposite affect as the addition of a polystyrene stiffening aid.

EXAMPLE 21

A two-layer laminate of a core and one skin layer was formed of Kraton TM 1107 (SIS)/Exxon TM polypropylene 3014. A Berlyn TM extruder operating at 6 RPM was used with the polypropylene and a Killion TM extruder operating at 125 RPM was used for the Kraton TM. The polymers were fed to an 18 inch(45.7 cm) 440° F.(227° C.) Cloeren TM die with one manifold shut down. The resulting film was cast on a roll at 60° C. and rotating at 35.2 RPM. The laminate formed was 2 mil(0.051 mm) thick with a core/skin ratio of 2.5:1 and exhibited a coarse microtexture when stretched 5:1 and allowed to recover instantly. Necking on subsequent restretching was only 2.5%.

EXAMPLE 22

A laminate was formed having skins of different compositions. The elastic core was Kraton TM 1107 with one polyethylene (Dow TM LLDPE 61800) and one polypropylene (Exxon TM 3085) skin. The core was extruded with a Berlyn TM extruder, while the skins were extruded with Rheotec TM and Brabender TM extruders, respectively. The Cloeren TM die was at 350° F.(177° C.) and the casting roll at 60° F.(16° C.). Two films were formed. For the first, the extruders operated at 20, 8 and 26 RMP's respectively while the cast roll operated at 17.3 RPM to form laminates with core/skin ratios of 18:1. The sample formed was instant shrink at a 5:1 stretch, with a fine microtexture. For the second film, the extruders and cast roll operated at 10, 16, 26 and 14.2 RMP's respectively to form a laminate with a core/skin ratio of 18:1. The second laminate was also instant shrink at 5:1 stretch yet exhibited coarse surface texture. Both laminated were 4.0 mil(0.1 mm) thick.

EXAMPLE 23

The laminate tape backing of Example 16 was stretched in a first direction by 8:1 and sequentially in a cross direction by 4:1. This laminate was of the instant shrink type.

EXAMPLE 24

The laminate of Example 3A was stretched in one first direction at 4:1 and sequentially in a cross direction by 4:1. This laminate was of the instant shrink type. The texture formed is shown in FIG. 10.

EXAMPLE 25

The laminate of 3A was stretched simultaneously biaxially at 4:1 by 4:1. The laminate recovered instantly. The core/skin thickness of unstretched laminate was 90/5 microns, respectively.

EXAMPLE 26

A three-layer laminate of polypropylene/SEBS(-Kraton TM 1657)/polypropylene used in Example 17 was tested for writability. The core/skin ratio was 5:1 with a total laminate thickness of 5 mil(0.13 mm). The film was stretched to 5:1 and allowed to recover. The writability before and after stretching is shown in FIGS. 7 and 8, respectively.

EXAMPLE 27

A series of LLDPE/SIS/LLDPE laminates were compared for their non-necking characteristics, as shown in Table XIII below.

TABLE XIII

| # | C/S RATIO | STRETCH RATIO | THICKNESS (microns) | % WIDTH CHANGE |
|---|---|---|---|---|
| A | 8.75 | 5:1 | 215 | 2.8 |
| B | 6.0 | 5:1 | 120 | 3.2 |
| C | 6.7 | 5:1 | 78 | 5.2 |
| D | 15.3 | 7:1 | 100 | 10.0 |
| E | 21.2 | 8:1 | 132 | 33.3 |
| F | PURE SIS | 5:1 | | 50.0 |
| G | " | 7:1 | | 62.5 |
| H | " | 8:1 | | 70.8 |

The first 3 examples are from Example 2, and SIS was also tested for comparison purposes. As the C/S ratio and stretch ratios rose, the problems with necking increased.

EXAMPLE 28

The use of adhesive cores was demonstrated. First a copolymer of isooctyl acrylate (IOA) and acrylic acid (AA) in monomer ratios of (90/10) was used as a core with polypropylene (Exxon TM 3014) and PET (intrinsic viscosity 0.62) as the skins in the first two examples. The IOA/AA copolymer was prepared in accordance with U.S. Pat. No. 4,181,752. The core/skin ratios and total thicknesses were 20 and 10, and 22 mil(0.56 mm) and 6 mil(0.15 mm) before lamination for the PP and PET examples, respectively. The laminates were cured for 5 minutes using a 15 watt UV light to cure the cores. The PP skin embodiment was an instant shrink at 500% stretch while the PET skin embodiment was a heat shrink laminate at 400% stretch.

PET was also used as a skin layer for a Kraton TM 1107 (56 parts) Wingtack Plus TM (35 parts) and Wingtack TM 10 (9 parts) core with a core/skin ratio of 83:1 and a total thickness of 25.6 mil(0.65 mm) before lamination. This laminate was of the instant shrink type at 400% stretch.

EXAMPLE 29

This example demonstrates skin controlled relaxation in the heat shrink region and control of the heat shrink mechanism by % elongation and core/skin ratio. A series of 5 mil(0.12 mm) laminates were made with a core of Kraton TM 1107 (89 parts) poly(alpha-methyl)styrene (10 parts) and Irganox TM (Ciba-Geigy Corp., Hawthorne N.Y.) (1 part-antioxidant). The skins were polypropylene (Exxon TM 3085). A Berlyn TM extruder was used for the core and Rheotec TM extruders for the skin using a Cloeren TM 3 layer feedblock and a 18 inches(45.7 cm) film die. The cast wheel temperature was 80° F.(27° C.) with the speed determined by the core/skin (C/S) ratio and the skin extruder speed. The shrink mechanism as a function of C/S ratio and % stretch is shown in FIG. 12. Fast is when more than 15% recovery occurred at 5 seconds. Medium time is where greater than 15% recovery occurred at 20 seconds. Slow time is where greater than 15% recovery was not noted until 60 seconds after stretch.

Figure 13:
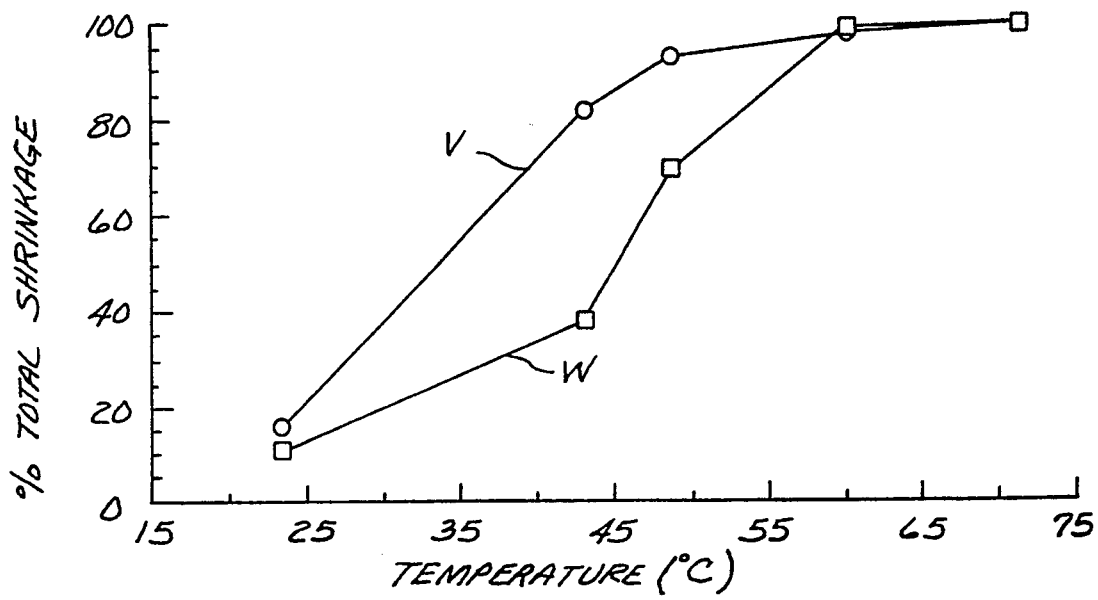
FIG. 13 is a diagram showing the relationship between the core/skin ratio, the percent of total recovery and activation temperature.

Skin control of the temperature of activation for the heat shrink material is demonstrated in FIG. 13. The temperature of activation is defined as the temperature required to achieve 50% or 90% of the recovery obtainable. Lines V and W represent samples with core/skin ratios of 4.71 and 4.11, respectively. As is seen, as the core/skin ratio went down the temperature of activation (both $T_{a-90}$ and $T_{a-50}$) went up, indicating a skin controlled relaxation. In this Figure, the 100% value is defined as the % shrinkage at 160° F.(71° C.), which for most practical purposes was the upper limit of available recovery. The points below 80° F.(27° C.) are the amounts of preactivation shrinkage for each example.

Three samples were also tested to measure the increase in opacity from the unstretched clear film as seen in Table XIV below.

TABLE XIV

| CORE/ SKIN* RATIO | % STRETCH | TEX- TURE | SHRINK MECHA- NISM | OPA- CITY AS CAST | OPACITY ACTI- VATED |
|---|---|---|---|---|---|
| 4.71 | 300 | C | H | 2.42% | 30.4% |
| 4.97 | 700 | F | I | 2.08 | 37.5 |

TABLE XIV-continued

| 5.0 | 300 | C | H | 3.40 | 35.8 |

*The core had a ½% blue pigment.

EXAMPLE 30

A foamed core three-layer film was made. The skins were Dow ™ LLDPE 6806 and the core was 99.5% Kraton ™ 1107 with 0.5% AZNP 130 blowing agent (Uniroyal Chemical Co., Naugatuck, Conn). Total film thickness was 20 mil(0.5 mm). The skins were 2.0 mil(0.05 mm) thick each. The foamed core specific gravity was 0.65 as compared to unfoamed Kraton ™ specific gravity of 0.92. A three-layer coextrusion die was used. This was an instant shrink sheet exhibiting a coarse texture at about 300% stretch.

EXAMPLE 31

The film from Example 2 with a core/skin ratio of 6:1 was characterized for its unstretched and stretched modulus value, the results of which are shown in FIG. 5; X is the Kraton ™ 1107 elastomer alone, ZZ is the polyethylene skin alone, Z is the laminate as cast and Y is the laminate after stretching to 500% and recovery.

EXAMPLE 32

The film laminate of certain examples were examined to determined the contact mechanism between the skin and core layers. The stretched and activated samples were cut with a razor blade on a hard surface. The samples were then examined at the cut edges with a scanning electron microscope. The core/skin contact was then determined visually with the results summarized in Table XV below.

TABLE XV

| Ex | Composition | Stretch Ratio | Comments |
| --- | --- | --- | --- |
| 5 | PVDF + PMMA/SIS/PVDF + PMMA | 2.2 | Elastic cohesive failure |
| 6 | PB/SIS/PB | 3 | Elastic cohesive failure |
| 7 | PE/EVA/SIS/EVA/PE | 5 | Adhesive failure |
| 12A | EVA/SIS/EVA | 4 | Adhesive failure |
| 12B | FA300/SIS/FA300 | 7 | Adhesive failure |
| 19E | PE/SIS + PS/PE | 3 | Some voids |
| 8 | LLDPE/SIS/LLDPE | 3 | Filled |
|  |  | 5 | Filled |
|  |  | 7 | Filled |
| 15A | PP/SEBS/PP | 4 | Filled |
| 15C | PP/SEBS/PP | 5.3 | Elastic cohesive failure |
| A | PP/SIS/PP | 5.0 | Filled |

New sample A corresponds to Example 29. Sample A had approximately the caliper of the Example 29 samples with a core/skin ratio of 5.1 and was a heat shrink laminate.

COMPARATIVE EXAMPLE 1

A three-layer film of Dow ™ LLDPE 2517 (Polyethylene)/Pebax ™ (Atomchem Co, France) 3533/LLDPE 2417 was made. The film was formed by pressing three precursor films together at 400° F.(204° C.) and about 2000 pounds of pressure(140 kg/sq.cm) for 5 minutes. The film formed was 5 mil(0.13 mm) thick with a core/skin ratio of 12.7. The laminate was stretched 400% (from 1 to 5 cm). The stretched laminate then contracted to 3.2 cm (36% of stretched length) at room temperature. The relaxed laminate was then heat shrunk by 180° F.(82° C.) air and it contracted to 1.5 cm (53% of relaxed length). An edge of the sample was then cut and observed for microtexturing. No folds were observed at 1000× magnification. Microscopic bumps, probably formed by recompression of the cover layer, and skin delamination was observed. The C.O.F. and opacity for the cast laminate was 0.901 and 2.77% while that for the relaxed activated laminate was 0.831 and 12.4%, respectively.

EXAMPLE 33

The tape constructions described in Table XVI were prepared with the laminate backing produced in accordance with the above described coextrusion techniques with the adhesive layer applied as disclosed. Adhesive was applied to the polypropylene side of the laminate. These tapes were then tested for properties such as peel from glass, peel from a microtextured tape backing (e.g., from itself), writability and conformability.

Conformability is a test of the force necessary for a substrate to deform into a curved surface using a matching bar. Conformability was tested using a Handle-O-Meter ™ (Model 210) available from Thwing-Albert Instrument Company, Philadelphia, Pa. The test was run with the film parallel with the slot in the machine direction (M.D.) of the film and the cross direction of the film. The film width in both cases was 4 inches(10.26 cm) and the slot width was set at ¼ inch(0.635 cm). The test was run with unstretched laminate, laminate uniaxially stretched and recovered in the M.D. and laminated biaxially stretched and recovered in the M.D. and C.D.

As summarized in Table XVIII, conformability is the force necessary to force the laminate fully into the slot with a corresponding bar. For uniaxially (M.D.) stretched films the formation of microstructure generally made the laminate more conformable to deformation in the machine direction yet reinforced the laminate to deformation in the cross direction (C.D.), i.e., made it more rigid. The result is a laminate having highly asymmetrical conformability. This is useful for a tape that is to be attached to a surface with a two dimensional curve (e.g., a pipe) where conformability in the flat direction is unneeded or undesirable.

For a multiaxially stretched laminate, conformability increases in both the M.D. and C.D.

The peel tests from glass and from the tape backsize were both performed according to ASTM 180° Peel Test D 3330-87 as reported in Table XVII. Disposable glass slides cleaned with ethyl acetate were used once for each reading. The tapes in the backsize test were placed M.D. to M.D. A 5 lb(2.3 kg) roller was used to adhere the tapes, with one pass at 90 in/min(2.3 m/min) with a 1 min dwell time. The tape was then attached to the jaw of an adhesion testing machine with a lower platen speed of 2.3 meters/min (90 in/min). Two second average readings were taken. In Table XVII, the numbers in parenthesis are readhesion tests, where the sample originally peel tested is readhered and retested for peel.

Writability was determined visually on a scale of poor (P), fair (F), good (G), very good (VG), and excellent (E). The ink was a water-based composition from a broad tip pen applied at normal hand pressure. Poor (P) writability indicates that the ink beaded immediately and easily wiped off the surface. Fair (F) indicates that the ink beaded up over time and could be partially wiped off. Good (G) indicates that the ink could not be wiped off, but that there was some blurring of the lines drawn. Very good (VG) indicates that ink could not be wiped off and that only a small amount of blurring occurred. Excellent (E) indicates that the ink could not be wiped off and that there was no perceivable blurring of the lines.

Writability appeared to clearly improve with uniaxial stretching and even more so with biaxial stretching.

Readhesion peel tests are second peel tests run on the same tape sample used in the first corresponding test. This is a measure of the repositionability of the tape.

The shrink mechanism, repositionability, and tamper indication mechanism of each tape sample is disclosed in Table XIX.

TABLE XVI

| EXP No. | CORE Comp. | Thick | SKIN Comp. | Thick | TIE Comp. | Thick | Coat | ADHESIVE Comp. | Thick |
|---|---|---|---|---|---|---|---|---|---|
| A | Kraton ™ 1107 | 100μ | Polypropylene(P.P) (3085) | 7.5μ 7.5 | — | — | I | X | 9.0μ |
| B | " | " | Polypropylene(P.P.) (3085) | " " | — | — | I | X | 14.0 |
| C | 90% Kraton ™ 1107 10% PAMS 18-210 | 75 | Polypropylene(P.P.) (3085) Polypropylene(P.P.) (3085) | 18.8 18.8 | — | — | I | X | 10.0 |
| D | Kraton ™ 1657 | 100 | Polypropylene(P.P.) (3085) | 25 25 | — | — | I | X | 37.5 |
| E | Kraton ™ 1107 | 125 | Polypropylene(P.P.) (3085) | 6.25 6.25 | — | — | II | Y | 37.5 |
| F | Kraton ™ 1107 | 75 | Polyethylene(P.E.) 3520 | 7.5 7.5 | EVA260 " | 5.0 5.0 | I | X | 14.0 |
| G | 85% Kraton ™ 1107 15% P.S. 685-26W | 70.0 | P.E. 6806 | 18.8 " | — | — | III | Y | 37.5 |
| H | Kraton ™ 1107 | 37.5 | P.E. 3010 | 12.5 " | EVA260 " | 5.0 5.0 | IV | Z | 12.50 |
| I | Kraton ™ 1107 | 90.0 | P.P. 3085 P.E. 61800 | 9.3 9.3 | — | — | I | X | 12.5 |
| J | " | 92.5 | P.P. 65F53 | 15.0 15.0 | | | III | Y | 37.5 |
| K | " | 70.0 | P.P. 15486 | 37.5 | — | — | X | W | 37.5 |
| L | P.U. 2363-75A | 18.75 | 50% PP 65F54 25% PB 0200 25% EVA 40W | 22.5 22.5 | | | I | X | 15.0 |
| M | Kraton ™ 1107 | 175.0 | 70% Solvay ™ 1008 30% PMMA VM100 | 12.5 12.5 | — | — | III | Y | 37.5 |
| N | " | " | 70% Solvay ™ 1008 30% PMMA VM100 | 12.5 12.5 | | | XI | Y | 37.5 |
| O | " | 75 | Polyester FA300 | 22.5 | | | I | X | 22.5 |
| P | " | 70.0 | 50% PB 0200 50% PB 0400 +CaCO3 contaminant | 10.0 10.0 | | | III | Y | 37.5 |
| Q | " | 55.0 | EVA 260 | 10.0 10.0 | | | III | Y | 37.5 |
| R | " | 50.0 | PP 3085 | 5.0 5.0 | | | XII | V | 55.0 |
| S | 80% PU-2352 —70A and 20% EVA 40W | 65.0 | PP 65F54 | 10.0 | | | III | Y | 37.5 |
| T | Kraton ™ 1107 | 150.0 | 50% PP 4092 and 50% Mineral Oil | 50.0 | | | III | Y | 37.5 |
| U | " | 55.0 | PS 685-26W | 7.5 7.5 | | | III | Y | 37.5 |
| V | P.U.2102-75A | 75.0 | P.E. 3150B 5% Kraton ™ 1107 | 5.0 5.0 | | | III | Y | 37.5 |
| W | Kraton ™ 1107 | 227.5 | PE 2517 | 20.0 | EVA 260 | 7.5 | XIII | X | 50–12.5μ |

TABLE XVI-continued

| EXP No. | CORE Comp. | Thick | SKIN Comp. | Thick | TIE Comp. | Thick | Coat | ADHESIVE Comp. | Thick |
|---|---|---|---|---|---|---|---|---|---|
|  |  |  |  | 20.0 | " | 7.5 |  |  |  |

PAMS 18-210; Poly(alpha-methyl)styrene 18-210 from Amoco, Chicago, IL.
Polyethylene 3520 and 3150B; available from Amoco, Chicago, IL.
EVA 260 and 40W; ethylenevinylacetate from E. I. Dupont de Nemours Co., Wilmington, DE.
P.S. 685-26W; polystyrene 685-26W available from Dow Chemical Co., Midland, MI.
P.E. 3010, 61800, 6806, and 2517; polyethylene from Dow Chemical Co., Midland, MI.
PP (polypropylene) 65F53 and 65F54; available from Himont U.S.A., Inc., Wilmington, DE.
polypropylene 15486; available from Charles B. Edwards, Minneapolis, MN
PB 0200 and 0400; polybutylene available from Shell Chemical Co.
Solvay $^{TM}$ 1008; polyvinylidenefluoride available from Soltex Polymer Corp., Houston TX
PMMA; VM100 polymethylmethacrylate available from Rohm & Haas, Philadelphia, PA.
Polyester FA300; available from Eastman Chemical Products, Inc., Kingsford, TN.
PU 2352-70A; polyurethane available from DuPont
PP 3085 and 4092; available from Exxon Chemical Co.
PU 2102-75A; polyurethane available from Dow Chemical.
X: 40% isooctyl acrylate-acrylic acid (IOA-AA) 95.5/4.5 and 60% Foral $^{TM}$ 85, Hercules, Wilmington, Del.
Y: 3M 9671SL, available from 3M Corp., St. Paul, MN.
Z: 50% Kraton $^{TM}$ 1107 and 50% Wingtack $^{TM}$ Extra with antioxidants
W: IOA-AA (94.5-5.5)
V: 96% IOA-AA (90-10) and 4% Irgacure 651, Ciba Geigy Corp. Hawthorne, NJ
I: solvent coat from a solution of two parts heptane to 1 part isopropyl alcohol onto the cast film
II: laminate to stretched film
III: laminate to cast film
IV: hot melt coat at 350° F. (177° C.)
X: coextrusion
XI: laminate to microtextured film
XII: coated onto cast film and U.V. cured for 5 min. at 15 watts
XIII: solvent coat microtextured film from 2 parts heptane to 1 part IPA
In Table VI of the solvent coated samples, sample I was dried in 90° F. oven for 1 min. All other solvent coated samples (A–D, F, L, O and T) were dried at room temperature for 24 hours.

TABLE XVII

| Sample Number | Draw Ratio | 180° Peel from Glass (N/25 mm) | | | 180° Peel for backside (N/25 mm) | | |
|---|---|---|---|---|---|---|---|
| | | As Cast Peel | Uniaxed Peel | Biaxed Peel | As Cast Peel | Uniaxed Peel | Biaxed Peel |
| A | 7.5 | 4.96 | 1.31 (1.32) | — | — | — | — |
| B | 7.5 | 3.74 | 1.38 (1.59) | 3.90 (3.51) | 1.58 | 0.73 | 0.65 |
| C | 5.0 | 2.51 A.T. | 0.46 (0.46) | — | 1.93 | 0.48 | — |
| D | 6.0 | 16.35 | 11.18 (9.07) | — | 10.32 | 5.92 | — |
| E | 7.0 | 6.91 A.T. | 9.72 (9.76) | — | 2.54 | 5.52 | — |
| F | 9.0 | 2.21 | 1.69 (1.73) | — | 1.72 | 1.09 | — |
| G | 7.5 | 7.77 | 3.92 (3.77) | — | — | — | — |
| H | 4.5 | 10.15 | 5.41 (4.36) | — | — | — | — |
| I | 5.0 | 7.26 | 5.22 (4.99) | 0.87 (0.86) | 1.46 | 2.50 | 2.65 |
| J | 3.5 | 9.75 | 9.88 (9.37) | — | 4.32 | 5.78 | — |
| K | 6.5 | 5.97 | 3.92 (4.42) | — | — | — | — |
| L | 3.0 | 6.07 A.T. | 4.94 (6.33) | — | 1.58 | 9.06 | — |
| M | 3.0 | 6.88 | 7.78 (7.80) | — | 3.82 | 3.75 | — |
| N | 3.0 | — | 7.24 (7.68) | — | — | — | — |
| O | 6.5 | 4.45 | 3.55 (3.03) | — | 2.88 | 1.15 | — |
| P | 2.0 | 8.14 | 7.67 (8.32) | — | 2.42 | 3.22 | — |
| Q | 4.5 | 4.93 | 5.63 (5.09) | — | 2.05 | 7.99 | — |
| R | 5.5 | 7.00 | 5.57 (5.38) | — | — | — | — |
| S | 0 | 11.77 D | — | — | — | — | — |
| T | 0 | 2.69 B | — | — | — | — | — |
| U | 0 | 0.14 D | — | — | — | — | — |
| V | 4.0 | 12.35 D | — | — | — | — | — |
| W | 7.0 | — | 1.45 (1.71) | 0.29 (0.27) | — | 0.16 | 0.17 |

D: delaminate
A.T.: adhesive transfer
B: breaks

TABLE XVIII

| Exp # | Water Based Ink Writability | | | Conformability (grams) | | | | | |
|---|---|---|---|---|---|---|---|---|---|
| | C | U | B | Cast MD | Cast CD | UMD | UCD | BMD | BCD |
| A | P | F | | | | | | | |
| B | P | F | VG | 106 | 96 | 146 | 17 | | |
| D | | | | 228 | 237 | | | | |
| F | P | G | | | | | | | |
| G | | | | 98 | 106 | 78 | 10 | | |
| H | | | | 22 | 23 | 44 | 4 | | |
| I | P | VG | E | 102 | 105 | 76 | 34 | 15 | 9 |
| J | P | VG | | 49 | 64 | 29 | 10 | | |
| K | P | F | | | | | | | |
| L | P | G | | 19 | 25 | 12 | 5 | | |

TABLE XVIII-continued

| Exp # | Water Based Ink Writability C | U | B | Conformability (grams) Cast MD | Cast CD | UMD | UCD | BMD | BCD |
|---|---|---|---|---|---|---|---|---|---|
| M | P | G | | | | | | | |
| O | P | G | | 593 | 599 | 158 | 44 | | |
| P | P | VG | | 52 | 58 | 19 | 8 | | |
| Q | F | G | | | | | | | |
| S | | | | 83 | 70 | | | | |
| T | | | | 753 | 698 | | | | |
| V | | | | 30 | 35 | | | | |
| W | F | VG | VG | 445 | 446 | 517 | 100 | 137 | 61 |

TABLE XIX

| EXP # | SHRINK MECHANISM | TAMPER MECHANISM | REPOSITION-ABILITY |
|---|---|---|---|
| A | I | rimple | Y |
| B | I | " | " |
| C | H | " | " |
| D | T | " | " |
| E | I | " | " |
| F | " | " | " |
| G | " | " | " |
| H | " | " | " |
| I | " | " | " |
| J | " | " | " |
| K | " | " | " |
| L | " | " | " |
| M | " | " | " |
| N | " | " | " |
| O | " | " | " |
| P | " | " | " |
| Q | " | " | " |
| R | " | " | " |
| S | " | delaminate | N |
| T | " | tear | N |
| U | " | delaminate | N |
| V | " | " | " |
| W | " | derimple | Y |

EXAMPLE 34

Sample I of Example 33 was further tested for peel adhesion at 90° and 0° as shown in Table XX. When the tape was removed from glass, it partially stretched with a 90° peel and fully stretched (i.e., to its natural draw) with a 0° peel. Generally, the 90° peel was less than the corresponding 180° peel except it was significantly higher for the biaxial peel from glass and slightly higher for the peel from backside test. It is believed the low 180° peel for biaxially stretched film is due primarily to the fine texture and high surface area that is formed with the sample. This will result in a low contact surface to glass at moderate rolldown pressures. In contrast, the microstructured backside will tend to intermesh with the microtextured adhesive layer and correspondingly will yield a higher peel from itself. It is believed that this intermeshing of microstructures is also responsible for the comparatively high peel from backsize values for both 90° and particularly 0°.

TABLE XX

| | Peel (N/25 mm) 90° | 0° |
|---|---|---|
| From Glass[1] | | |
| Cast peel | 3.60 | 10.30 |
| Readhesion | 2.59[2] | 6.64[3] |
| Uniaxed Peel | 3.26 | 6.64 |
| Readhesion | 2.66 | 6.16 |
| Biaxed Peel | 2.47 | |
| Readhesion | 2.22 | |
| From Backside | | |
| Cast Peel | 1.77 | 6.87[4] |
| Uniaxed Peel | 2.52 | 16.74 |
| Biaxed Peel | 2.78 | |

[1] All peel values are in Newtons/25 mm
[2] The tape stretched slightly when removed the first time
[3] The tape fully stretched when removed the first time
[4] The tape broke

EXAMPLE 35

Samples I and W were further peeled tested at 0°, 90° and 180° varying the rolldown force used to adhere the tape to the substrate from which it was peeled. The same ASTM test as described in Example 33, using a IMASS ™ 3M90(available from IMASS Inc., Hingham, Mass.). However, tape was applied and tested first with a 5 lb(2.3 Kg) roller at 90 in/min(2.3 m/min) with only one pass and tested second with a 10 lb(4.5 Kg) rolldown. The results in Newtons/25 mm are shown in Table XX.

The tapes of samples A, B, C and D were prepared using the laminate backings of samples I and W of Example 32 for (A and B) and (C and D), respectively. The adhesive system applied was X of Example 32 applied by solvent coating in a solution of two parts heptane and one part isopropyl-alcohol. Samples A and C had an adhesive layer thickness of 22.2μ, while that for sample B and D was 29.6μ.

Again, a wide variation in adhesive values were obtained for the stretched and activated tape lamination. The variations are due to the microstructure formed and final adhesive layer thickness. All the samples were solvent-coated and dried at room temperature for 24 hours. However, one generally noted trend is that the relative increase in peel was much higher for activated tape than that for cast tapes when the rolldown pressure was increased (excluding the cases where there was adhesive transfer(AT) or delamination(D)).

TABLE XXI

| Example No. | 0° 5lb | 10lb | 90° 5lb | 10lb | 180° 5lb | 10lb |
|---|---|---|---|---|---|---|
| A on glass | | | | | | |
| Cast | 16.5AT | 15.9 ATD | 3.4AT | 1.4AT | 3.6AT | 2.5AT |
| Uniax | 13.2AT | 13.4 ATD | 3.5 | 4.2 | 1.2 | 3.0 |
| Biax | 4.8D | 10.7D | 4.1 | 4.5 | 0.9 | 1.2 |
| A on A | | | | | | |
| Cast | >18.2 | 16.6 | 1.1 | 1.2 | 1.3 | 0.9 |

TABLE XXI-continued

| Example No. | 0° 51b | 0° 101b | 90° 51b | 90° 101b | 180° 51b | 180° 101b |
|---|---|---|---|---|---|---|
| Uniax | 7.1 | 11.2 | 2.1 | 3.6 | 2.1 | 2.7 |
| Biax | 2.8 | 2.8 | 2.5 | 3.7 | 0.3 | 0.4 |
| B on glass | | | | | | |
| Cast | 10.2 | 11.9 ATD | 2.0AT | 3.3AT | 2.9AT | 3.0AT |
| Uniax | 22.9 | 26.4 | 2.3 | 2.4 | 5.0 | 5.1 |
| Biax | 6.0 | 6.8 | 1.9 | 2.5 | 1.1 | 1.9 |
| B on B | | | | | | |
| Cast | 17.6AT | 15.7 ATD | 0.9 | 0.7 | 1.0 | 0.9 |
| Uniax | 6.3 | 9.1 | 0.9 | 1.3 | 2.0 | 2.3 |
| Biax | 6.8 | 8.6 | 1.0 | 1.5 | 1.4 | 2.6 |
| C on glass | | | | | | |
| Cast | 12.6AT | >18.2AT | 0.6 | 0.7 | 2.0AT | 1.0AT |
| Uniax | 14.5AT | 9.7 | 0.7 | 1.4 | 1.9 | 0.5 |
| Biax | 10.3 | 10.1 | 0.2 | 0.5 | 0.8 | 0.9 |
| C on C | | | | | | |
| Cast | 13.5 | 17.5 | 0.3 | 0.4 | 1.1 | 1.0 |
| Uniax | 9.1 | 9.2 | 0.2 | 0.5 | 0.6 | 0.8 |
| Biax | 0.9 | 2.2 | 0.06 | 0.4 | 0.2 | 0.2 |
| D on glass | | | | | | |
| Cast | >18.AT | >18.2AT | 7.0AT | 5.9AT | 8.1AT | 8.7AT |
| Uniax | 34.4AT | 16.5AT | 6.8 | 7.9 | 9.4 | 10.9 |
| Biax | 17.1 | >18.2 | 6.0 | 6.1 | 6.2 | 7.1 |
| D on D | | | | | | |
| Cast | >18.2 | Broke | 0.9 | 1.2 | 2.3 | 2.4 |
| Uniax | 14.4 | 16.3 | 2.3 | 3.4 | 4.9 | 5.1 |
| Biax | 13.0 | 17.2 | 3.5 | 4.4 | 3.1 | 4.5 |

EXAMPLE 36

Laminate tape backings with polystyrene were made in accordance with the procedures outlined in the above examples. The skins comprised polypropylene (Exxon TM 3014) with a Kraton TM 1107 based core for a three layer construction. Sample A had no polystyrene in the core, while samples B, C and D had 20%, 35% and 50% polystyrene (Dow Chemical Co. 685W), respectively. All had core/skin ratios of approximately 7:1. The tape laminates were laminated with a 1 mil acrylic adhesive (RD-975—available from 3M Co.). The samples were tested for 0° peel from glass using the procedures outlined above. However, the rolldown was once with a 5 lb(2.27 kg) roller, and testing was performed on an IMASS TM 3M90 Peel Tester. The peel was tested with the as cast tape laminate, and then with readhesion of the same tape a second and third time. Each measurement is an average of three test runs. The readhered runs 2 and 3, as shown in Table XXII, have significantly lower peel values particularly at low polystyrene content. This indicates the degree of stretch activation initiated in the prior 0° peel test.

TABLE XXII

| Sample Number | Thickness mils(mm) | 0° Peel(1) N/25 mm | 0° Peel(2) N/25 mm | 0° Peel(3) N/25 mm |
|---|---|---|---|---|
| A | 3.5(0.089) | 13.0 | 6.6 | 6.16 |
| B | 4.1(0.104) | 16.0 | 7.71 | 7.95 |
| C | 4.1(0.104) | 21.4 | 21.0 | 15.5 |
| D | 4.3(0.109) | 26.7 | 26.4 | 22.3 |

The percent stretch, here the percent increase in length over that of the original sample, and percent recovery, of the stretched length, for each peel are set forth in Table XXIII.

TABLE XXIII

| Sample Number | First Peel Stretch | First Peel Recovery | Second Peel Stretch | Second Peel Recovery | Third Peel Stretch | Third Peel Recovery |
|---|---|---|---|---|---|---|
| A | 645% | 89.5% | 645% | 89.5% | 645% | 89.5% |
| B | 485% | 89.7% | 485% | 89.7% | 485% | 89.7% |
| C | 330% | 79.5% | 430% | 72% | 430% | 72.0% |
| D | 250% | 58.0% | 270% | 59.3% | 270% | 59.3% |

EXAMPLE 37

The tape of Example 33, sample E, was stretched to its ultimate draw ratio. The tape was allowed to immediately recover. The tape was then cut on edge and is shown in FIG. 17.

EXAMPLE 38

Figure 16:
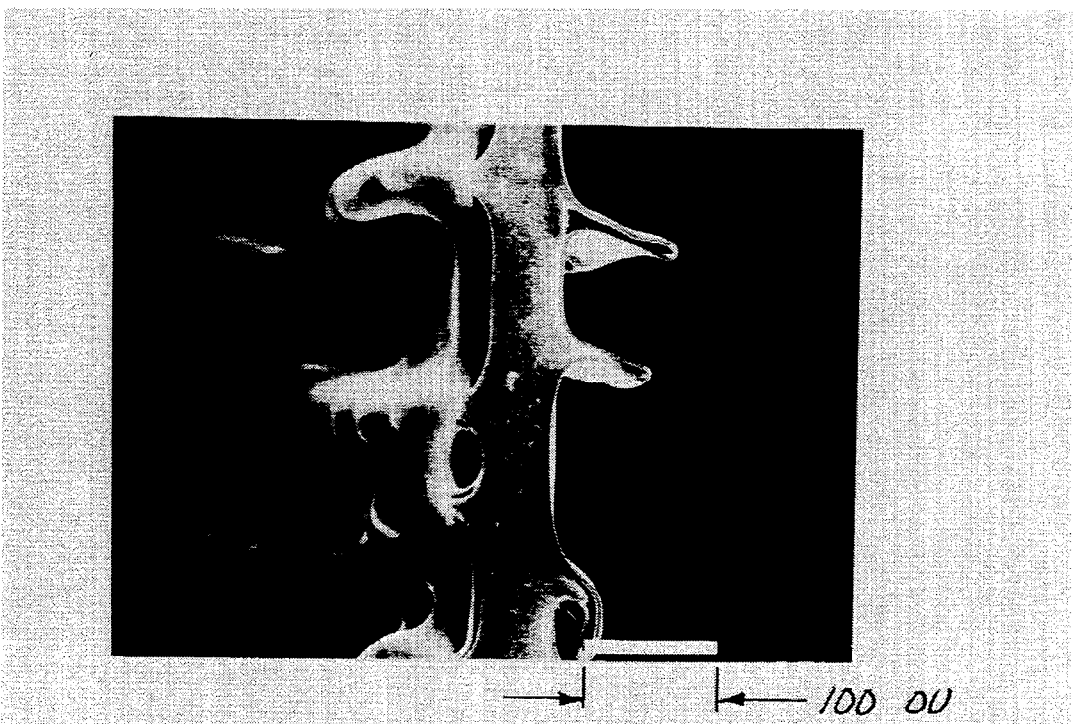
FIG. 16 is a scanning electron micrograph (200×) of a tape having a thin adhesive layer which forms an undulating surface.

A tape with a Kraton TM 1107 core and polypropylene skins (PP3085) was laminated with an acrylate adhesive 3M 9458, available from 3M Corporation, St. Paul, Minn., The original adhesive was 1 mil(25.4μ) thick. The tape was stretched to its ultimate draw ratio with the results shown in FIG. 16.

EXAMPLE 39

A sample having the layer composition of Example 27 (with 1% blue pigment in the core) was formed with an overall caliper of 3.0 mil(0.076 mm) and a core/skin ratio of 5.1:1. The film was cast onto a chrome casting wheel with a rubber nip. The 60° gloss was measured using ASTM D 2457-70 using a Gardner Instruments(-Bethesda, Md.) 60° gloss tester. The results are summarized in Table XXIV below for the as cast and three microtextured films (with different stretch rates).

TABLE XXIV

| | | 60° Gloss MD | 60° Gloss CD |
|---|---|---|---|
| As Cast | Chrome Side | 86 | 88 |
| | Rubber Side | 3.4 | 3.3 |
| 300% | Chrome Side | 2.1 | 3.5 |
| | Rubber Side | 1.5 | 1.9 |
| 400% | Chrome Side | 2.0 | 6.6 |
| | Rubber Side | 1.6 | 2.4 |
| 500% | Chrome Side | 2.2 | 3.0 |
| | Rubber Side | 1.6 | 1.8 |

EXAMPLE 40

Laminates from Example 32 were tested for layer adhesion using a variation of 180° peel test ASTM D 3330-87. Laminate (0.75 in, 1.9 cm) was placed between two pieces of masking tape (3M-2503, available from 3M Co., St. Paul, Minn.) of the same width. Tabs of one tape piece were adhered to the peel tester platen with additional pieces of masking tape. The three layers were pressed together with four passes of a 5 pound(2.3 Kg)

roller and allowed to sit for 10 minutes. The leading edge of the upper piece of masking tape was attached to the jaws of a peel tester leaving 0.5 in(1.27 cm) of masking tape to masking tape contact at the leading edge. The peel tester was run at 90 in(228.6 cm)/min. The results are set out in Table XXV below.

TABLE XXV

| Ex | 180° Peel (N/25 mm) | Delamination |
|---|---|---|
| 5 | 10.2 | No |
| 6 | 14.8 | No |
| 7 | 12.1 | Yes |
| 12A | 15.3 | Yes |
| 12B | 14.1 | Yes |
| 32A | 19.7 | No |

The various modifications and alterations of this invention will be apparent to those skilled in the art without departing from the scope and spirit of this invention, and this invention should not be restricted to that set forth herein for illustrative purposes.

We claim:

1. An elastomeric laminate tape consisting essentially of an elastomeric laminate comprised of at least one elastomeric layer and at least one outer skin layer wherein the at least one skin layer has a microtextured skin layer surface formed by inelastic deformation of the at least one skin layer in more than one direction and at least one substantially continuous pressure-sensitive adhesive layer in continuous contact with said at least one skin layer of said laminate.

2. The elastomeric laminate tape of claim 1 wherein the deformation of the at least one skin layer is created by sequential biaxial stretching.

3. The elastomeric laminate tape of claim 1 wherein the at least one skin layer having undergone inelastic deformation is an outer layer adjacent to said at least one adhesive layer.

4. The elastomeric laminate tape of claim 1 wherein said at least one adhesive layer has an undulating outer surface substantially corresponding to an adjacent underlying skin layer.

5. The elastomeric laminate tape of claim 4 wherein said at least one adhesive layer is less than 30 microns thick.

6. The elastomeric laminate tape of claim 1 comprising a removable label having a non-adhesive coated outer skin layer.

7. An elastomeric laminate tape comprising an elastomeric laminate comprised of at least one elastomeric core layer and at least one outer skin layer wherein the at least one skin layer has a microtextured skin layer surface formed by inelastic deformation of the at least one skin layer in at least one direction and at least one substantially continuous pressure-sensitive adhesive layer in continuous contact with at least the face of said laminate with the microtextured skin layer, wherein the adhesive thickness is such that its outer surface has an undulating texture corresponding to that of the underlying microtextured skin layer.

8. The elastomeric laminate tape of claim 7 wherein the surface area of the at least one microtextured skin layer is at least 50% greater than a corresponding untextured surface.

9. The elastomeric laminate tape of claim 8 comprising at least two skin layers each having microtextured surfaces said at least two skin layers comprising outer layers of said laminate.

10. The elastomeric laminate tape of claim 7 wherein the adhesive layer thickness is less than 30 microns.

11. The elastomeric laminate tape of claim 8 wherein said at least one core and said at least one skin layers are in continuous contact.

12. The elastomeric laminate tape of claim 8 wherein said at least one skin and adjacent at least one core layers are in intermittent contact.

13. An elastomeric laminate tape comprising an elastomeric laminate consisting essentially of at least one elastomeric layer and at least one outer skin layer wherein the at least one skin layer has a microtextured skin layer surface formed by inelastic deformation of the at least one skin layer in at least one direction and at least one substantially continuous pressure-sensitive adhesive layer over at least the entire face of said laminate with the microtextured skin layer, wherein the adhesive layer and the underlying skin layer are in substantially continuous contact providing improved anchorage of the adhesive layer to the laminate.

14. The elastomeric laminate tape of claim 13 wherein the deformation of the at least one skin layer is created by biaxial stretching.

15. The elastomeric laminate tape of claim 14 wherein the surface area of the at least one microtextured skin layer is at least 50% greater than a corresponding untextured surface.

16. The elastomeric laminate tape of claim 15 comprising at least two skin layers each having a microtextured skin layer surface said at least two skin layers comprising outer layers of said laminate.

17. The elastomeric laminate tape of claim 15 wherein said at least one adhesive layer on said at least one microstructured skin has a thickness such that the adhesive layer retains a substantially flat outer surface.

18. The elastomeric laminate tape of claim 17 wherein said at least one adhesive layer is greater than 30 microns thick.

19. The elastomeric laminate tape of claim 17 wherein said at least one core and said at least one skin layers are in continuous contact.

20. The elastomeric laminate tape of claim 17 wherein said at least one skin and adjacent at least one core layer are in intermittent contact.

* * * * *

UNITED STATES PATENT AND TRADEMARK OFFICE
CERTIFICATE OF CORRECTION

PATENT NO.: 5,354,597
DATED: October 11, 1994
INVENTOR(S): Karen M. Capik et al.

It is certified that error appears in the above-identified patent and that said Letters Patent is hereby corrected as shown below:

Col. 1, Line 11, "end" should read --and--;
Col. 3, Line 1, "X" should read --x--;
Col. 3, Line 9, "X" should read --x--;
Col. 3, Line 18, "X" should read --x--;
Col. 3, Line 21, "X" should read --x--;
Col. 3, : lines 34 and 37, "X" should read --x--.
Col. 16, Line 67, "3,175" should read --3.175--;
Col. 24, Line 37, "AS" should read -- As --.

Signed and Sealed this

Fourth Day of March, 1997

Attest:

BRUCE LEHMAN

Attesting Officer

Commissioner of Patents and Trademarks